(12) United States Patent
Hunicke-Smith et al.

(10) Patent No.: US 9,708,654 B2
(45) Date of Patent: Jul. 18, 2017

(54) HIGH THROUGHPUT SEQUENCING OF MULTIPLE TRANSCRIPTS

(71) Applicant: THE BOARD OF REGENTS OF THE UNIVERSITY OF TEXAS SYSTEM, Austin, TX (US)

(72) Inventors: Scott Hunicke-Smith, Austin, TX (US); Brandon Dekosky, Austin, TX (US); Andy Ellington, Austin, TX (US); George Georgiou, Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 35 days.

(21) Appl. No.: 14/407,849

(22) PCT Filed: Jun. 17, 2013

(86) PCT No.: PCT/US2013/046130
§ 371 (c)(1),
(2) Date: Dec. 12, 2014

(87) PCT Pub. No.: WO2013/188872
PCT Pub. Date: Dec. 19, 2013

(65) Prior Publication Data
US 2015/0141261 A1 May 21, 2015

Related U.S. Application Data

(60) Provisional application No. 61/660,370, filed on Jun. 15, 2012.

(51) Int. Cl.
*C12Q 1/68* (2006.01)
*B01L 3/00* (2006.01)
*C12N 15/10* (2006.01)

(52) U.S. Cl.
CPC ...... *C12Q 1/6869* (2013.01); *B01L 3/502784* (2013.01); *C12N 15/1075* (2013.01); *C12Q 1/6806* (2013.01); *B01L 2200/0647* (2013.01); *B01L 2200/0673* (2013.01)

(58) Field of Classification Search
CPC ............ C12Q 2535/122; C12Q 1/6806; C12Q 1/6869; C12Q 2547/101; C12Q 2563/149; C12Q 2563/159; B01L 2200/0647; B01L 2200/0673; B01L 3/502784; C12N 15/1075
See application file for complete search history.

(56) References Cited

U.S. PATENT DOCUMENTS

| | | | | |
|---|---|---|---|---|
| 9,304,065 B2* | 4/2016 | Fowler | ................... | C12Q 1/686 |
| 2005/0272039 A1 | 12/2005 | Yasuda | | |
| 2006/0233812 A1 | 10/2006 | Burnie et al. | | |
| 2007/0172887 A1 | 7/2007 | Takacs et al. | | |
| 2007/0281313 A1 | 12/2007 | Taniguchi et al. | | |
| 2009/0098555 A1 | 4/2009 | Roth et al. | | |
| 2011/0312505 A1* | 12/2011 | Reddy | ................. | C07K 16/065 506/2 |
| 2012/0308555 A1 | 12/2012 | Polakiewicz et al. | | |
| 2012/0312505 A1 | 12/2012 | Youbi-Idrissi et al. | | |
| 2013/0178370 A1 | 7/2013 | Lavinder et al. | | |
| 2014/0057799 A1 | 2/2014 | Johnson | | |

FOREIGN PATENT DOCUMENTS

| | | | |
|---|---|---|---|
| GB | 2502577 | * | 4/2013 |
| JP | 2004-81084 | | 3/2004 |
| JP | 2007-505611 | | 3/2007 |
| JP | 2007-319028 | | 12/2007 |
| JP | 2009-284834 | | 12/2009 |
| JP | 2010-535150 | | 11/2010 |
| WO | WO 03/052416 | | 6/2003 |
| WO | WO 2005/042774 | | 5/2005 |
| WO | WO 2005/084134 | | 9/2005 |
| WO | WO 2008/079914 | | 7/2008 |
| WO | WO 2008/104184 | | 9/2008 |
| WO | WO 2009/100896 | | 8/2009 |
| WO | WO 2010/083456 | | 7/2010 |
| WO | WO 2011/146514 | | 11/2011 |
| WO | WO 2012/061412 | | 5/2012 |
| WO | WO 2012/072705 | | 6/2012 |
| WO | WO 2012/083225 | | 6/2012 |

OTHER PUBLICATIONS

Arnaout, "Specificity and overlap in gene segment-defined antibody repertoires," *BMC Genomics*, 6:148, 2005.
Behrendt et al., "The role of somatic mutation in determining the affinity of anti-DNA antibodies," *Clin Exp Immunol*, 131:182-189, 2003.
Boudinot et al., "New perspectives for large-scale repertoire analysis of immune receptors," *Molecular Immunology*, 45:2437-2445, 2008.
Boyd et al., "Measurement and clinical monitoring of human lymphocyte clonality by massively parallel V-D-J pyrosequencing," *Science Translational Medicine*, 1(12):12ra23, 2009.
Burgoon et al., "Laser-capture microdissection of plasma cells from subacute sclerosing panencephalitis brain reveals intrathecal disease-relevant antibodies," *PNAS*, 102(20):7245-7250, 2005.
Campbell et al.,"Subclonal phylogenetic structures in cancer revealed by ultra-deep sequencing," *PNAS*, 105(35):13081-13086, 2008.
Chapal et al., "Thyroid peroxidase autoantibodies obtained from random single chain Fv libraries contain the same heavy/light chain combinations as occur in vivo," *Endocrinology*, 142(11):4740-4750, 2001.

(Continued)

*Primary Examiner* — Cynthia B Wilder
(74) *Attorney, Agent, or Firm* — Parker Highlander PLLC

(57) ABSTRACT

The present disclosure generally relates to sequencing two or more genes expressed in a single cell in a high-throughput manner. More particularly, the present disclosure relates to a method for high-throughput sequencing of pairs of transcripts co expressed in single cells (e.g., antibody VH and VL coding sequence) to determine pairs of polypeptide chains that comprise immune receptors.

20 Claims, 10 Drawing Sheets

(56) References Cited

OTHER PUBLICATIONS

Cheung et al., "A proteomics approach for the identification and cloning of monoclonal antibodies from serum", *Nature Biotechnology*, 30(5):447-52, 2012.
Clackson et al., "Making antibody fragments using phage display libraries," *Letters to Nature*, 352:624-628, 1991.
Correia-Neves et al., "The shaping of the T cell repertoire," *Immunity*, 14:21-32, 2001.
Damoc et al., "High resolution proteome analysis of cryoglobulins using Fourier transform-ion cyclotron resonance mass spectrometry", *Proteomics*, 3:1425-1433, 2003.
De Costa et al., "Sequencing and quantifying IgG fragments and antigen-binding regions by mass spectrometry," *Journal of Proteome Research*, 9:2937-2945, 2010.
DeKosky et al., "High-throughput sequencing of the paired human immunoglobulin heavy and light chain repertoire", *Nature Biotechnology*, 31(2):166-169, 2013.
Dornmair et al., "Novel approaches for identifying target antigens of autoreactive human B and T cells", *Seminars in Immunopathology*, 3 1(4):467-477, 2009.
Fischer et al., "Sequencing antibody repertoires: the next generation", *MAbs*, 3(1):17-20, 2011.
Freeman et al., "Profiling the T-cell receptor beta-chain repertoire by massively parallel sequencing," *Genome Research*, 19:1817-1824, 2009.
Glanville et al., "Precise determination of the diversity of a combinatorial antibody library gives insight into the human immunoglobulin repertoire", *Proc Natl Acad Sci USA*, 106(48):20216-20221, 2009.
Huse et al., "Purification of antibodies by affinity chromatography", *J Biochem Biophys Methods*, 51:217-231, 2002.
Instructions for Product Nos. 21901 and 21902, Maleimide-PEG2-Biotin Sulfhydryl-reactive biotin labeling reagent with polyethylene glycol (PEG) spacer arm, published by Thermo Fisher Scientific, Inc., 2008.
International Invitation to Pay Additional Fees issued in International Application No. PCT/US2013/046130, mailed Sep. 4, 2013.
International Preliminary Report on Patentability issued in International Application No. PCT/US2013/046130, mailed Dec. 24, 2014.
International Search Report and Written Opinion issued in International Application No. PCT/US2013/046130, mailed Nov. 15, 2013.
Ippolito et al., "Antibody repertoires in humanized NOD-scid-IL2Rγ(null) mice and human B cells reveals human-like diversification and tolerance checkpoints in the mouse", *PLoS One*, 7(4):e35497, 2012.
Kurokawa et al., "Paired cloning of the T cell receptor α and β genes from a single T cell without the establishment of a T cell clone," *Clin Exp Immunol*, 123:340-345, 2001.
Maiolica et al., "Targeted proteome investigation via selected reaction monitoring mass spectrometry", *Journal of Proteomics*, 75(12):3495-3513, 2012.
Matsutani et al., "Restricted usage of T-cell receptor α-chain variable variable region (TCRAV) and T-cell receptor β-chain variable region (TCRBV) repertoires after human allogeneic haematopoietic transplantation," *British Journal of Haematology*, 109:759-769, 2000.
McMahan et al., "Production, characterization, and immunogenicity of a soluble rat single chain T cell receptor specific for an encephalitogenic peptide," *The Journal of Biological Chemistry*, 278(33):30961-30970, 2003.
Meijer et al., "Isolation of human antibody repertoires with preservation of the natural heavy and light chain pairing", *Journal of Molecular Biology*, 358(3): 764-772, 2006.
Meijer et al., "Isolation of human antibody repertoires with preservation of the natural heavy and light chain pairing", *Journal of Molecular Biology*, 358(3): 764-772, 2006. (Supplementary Data)
Mouquet et al., "Complex-type N-glycan recognition by potent broadly neutralizing HIV antibodies", *Proc Natl Acad Sci USA*, 109(47):E3268-E3277, 2012.
Nazabal et al., "Immunoassays with direct mass spectrometric detection", *Analytical Chemistry*, 78(11):3562-3570, 2006.
Obermeier et al., "Matching of oligoclonal immunoglobulin transcriptomes and proteomes of cerebrospinal fluid in multiple sclerosis," *Nature Medicine*, 14(6):688-693, 2008.
Office Communication issued in corresponding European Application No. 13733180.7, dated Sep. 24, 2015.
Omenn et al., "Overview of the HUPO plasma proteome project: results from the pilot phase with 35 collaborating laboratories and multiple analytical groups, generating a core dataset of 3020 proteins and a publicly-available database", *Proteomics*, 5:3226-3245, 2005. [Supplementary Materials, Protein dateset].
Packer and Muraro, "Optimized clonotypic analysis of T-cell receptor repertoire in immune reconstitution," *Experimental Hematology*, 35:516-521, 2007.
Peng, "Protein mixture analysis by tandem mass spectrometry" In: The Bioinformatics of Brains: From Genes and Proteins to Behaviors (Williams RW, ed.), pp. 61-68 (2003), Washington, DC: Society for Neuroscience.
Persson et al., "Generation of diverse high-affinity human monoclonal antibodies by repertoire cloning," *Proc. Natl. Acad. Sci. USA*, 88:2432-2436, 1991.
Ravetch et al., "Structure of the human immunoglobulin mu locus: characterization of embryonic and rearranged J and D genes", *Cell*, 27:583-591, 1981.
Reddy et al., "Monoclonal antibodies isolated without screening by analyzing the variable-gene repertoire of plasma cells", *Nature Biotechnology*, 28(9):965-9, 2010.
Sato et al., "Proteomics-directed cloning of circulating antiviral human monoclonal antibodies", *Nature Biotechnology*, 30(11):1039-1043, 2012.
Schluter et al., "Sequence analysis of homogeneous peptides of shark immunoglobulin light chains by tandem mass spectometry: correlation with gene sequence and homologies among variable and constant region peptides of sharks and mammals," *Molecular Immunology*, 27(1):17-23, 1990.
Tanaka et al., "Single -cell analysis of T-cell receptor repertoire of HTLV-1 tax-specific cytotoxic T-cells in allogeneic transplant recipients with adult T-cell leukemia/lymphoma", *Cancer Research*, 70(15): 6181-6192, 2010.
Weinstein et al., "High-throughput sequencing of the zebrafish antibody repertoire," *Science*, 324:807-810, 2009.
Willis et al., "Rapid molecular cloning of rearrangements of the IGHJ locus using long-distance inverse polymerase chain reaction", *Blood*, 90(6):2456-2464, 1997.
Wine et al., "Molecular deconvolution of the monoclonal antibodies that comprise the polyclonal serum response", *Proc Natl Acad Sci USA*, 110(8):2993-2998, 2013.
Yates, "Mass spectrometry from genomics to proteomics", *Trends Genet.*, 16(1):5-8, 2000.
Kumaresan et al., "High-throughput single copy DNA amplification and cell analysis in engineered nanoliter droplets," *Analytical Chemistry*, 80 (10):3522-3529, 2008.
Mary et al.,"Analysis of gene expression at the single-cell level using microdroplet-based microfluidic technology," *Biomicrofluidics*, 5:024109, 2011.
Novak et al.,"Single-cell multiplex gene detection and sequencing with microfluidically generated agarose emulsions," *Angew. Chem. Int. Ed.*, 50:390-395, 2011.
Zhang et al., "Massively parallel single-molecule and single-cell emulsion reverse transcription polymerase chain reaction using agarose droplet microfluidics," *Analytical Chemistry*, 84:3599-3605, 2012.

\* cited by examiner

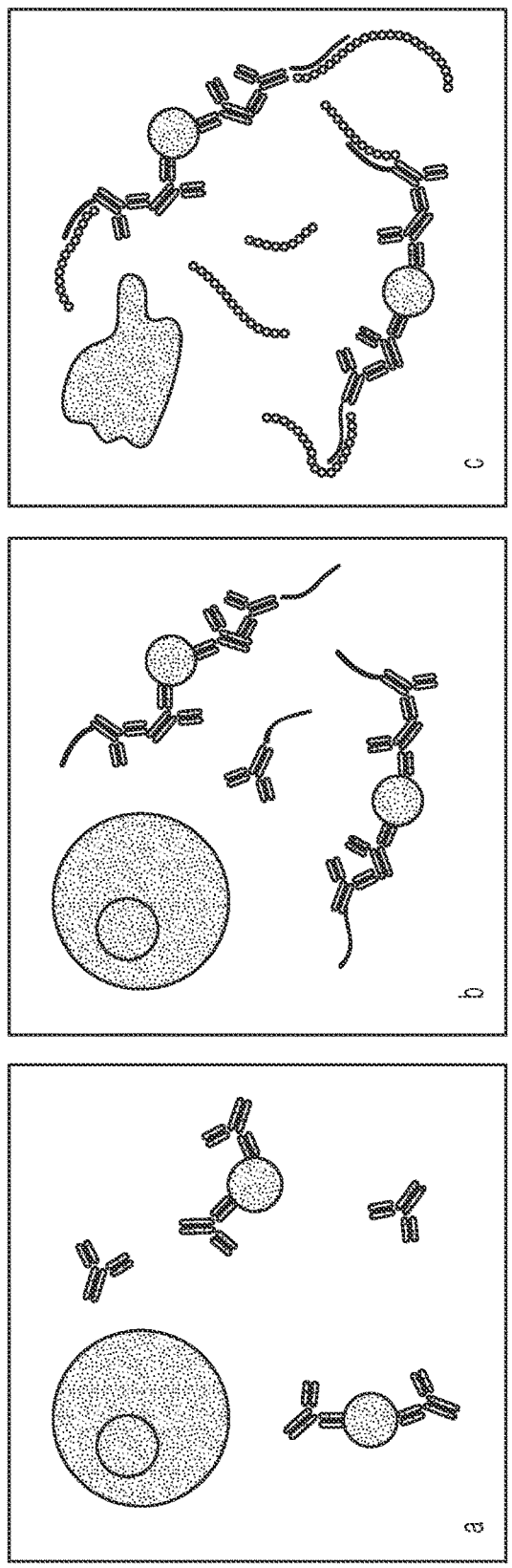

HIGH THROUGHPUT SEQUENCING OF MULTIPLE TRANSCRIPTS

The present application is a national phase application under 35 U.S.C. §371 of International Application No. PCT/US2013/046130, filed Jun. 17, 2013, which claims the priority benefit of U. S. provisional application No. 61/660,370, filed Jun. 15, 2012, the entire contents of each of which are incorporated herein by reference.

BACKGROUND OF THE INVENTION

1. Field of the Invention

The present invention relates generally to the field of molecular biology and immunology. More particularly, it concerns methods for high-throughput isolation cDNAs encoding immune cell receptors and antibodies.

2. Description of Related Art

There is a need to identify the expression of two or more transcripts from individual cells at high throughput. In particular, for numerous biotechnology and medical applications it is important to identify and sequence the gene pairs encoding the two chains comprising adaptive immune receptors from individual cells at a very high throughput in order to accurately determine the complete repertoires of immune receptors expressed in patients or in laboratory animals. Immune receptors expressed by B and T lymphocytes are encoded respectively by the VH and VL antibody genes and by TCR α/β or γ/δ chain genes. Humans have many tens of thousands or millions of distinct B and T lymphocytes classified into different subsets based on the expression of surface markers (CD proteins) and transcription factors (e.g., FoxP3 in the Treg T lymphocyte subset). High-throughput DNA sequencing technologies have been used to determine the repertoires of VH or VL chains or, alternatively, of TCR α and β in lymphocyte subsets of relevance to particular disease states or, more generally, to study the function of the adaptive immune system (Wu et al., 2011). Immunology researchers have an especially great need for high throughput analysis of multiple transcripts at once.

Currently available methods for immune repertoire sequencing involve mRNA isolation from a cell population of interest, e.g., memory B-cells or plasma cells from bone marrow, followed by RT-PCR in bulk to synthesize cDNA for high-throughput DNA sequencing (Reddy et al., 2010; Krause et al., 2011). However, heavy and light antibody chains (or α and β T-cell receptors) are encoded on separate mRNA strands and must be sequenced separately. Thus, these available methods have potential to unveil the entire heavy and light chain immune repertoires individually, but cannot yet resolve heavy and light chain pairings at high throughput. Without multiple-transcript analysis at the single-cell level to collect heavy and light chain pairing data, the full adaptive immune receptor, which includes both chains, cannot be sequenced or reconstructed and expressed for further study.

SUMMARY OF THE INVENTION

In a first embodiment, the present invention provides a method comprising (a) sequestering single cells and an mRNA capture agent into individual compartments; (b) lysing the cells and collecting mRNA transcripts with the mRNA capture agent; (c) isolating the mRNA from the compartments using the mRNA capture agent; (d) performing reverse transcription followed by PCR amplification on the captured mRNA; and (e) sequencing at least two distinct cDNA products amplified from a single cell. In certain aspects, the cells may be B cells (e.g., plasma cells or memory B cells), T cells, NKT cells, and cancer cells.

Thus, in a specific embodiment, the present invention provides a method for obtaining a plurality of paired antigen receptor sequences comprising: (a) isolating single mammalian cells in individual compartments with immobilized oligonucleotides for priming of reverse transcription; (b) lysing the cells and allowing mRNA transcripts to associate with the immobilized oligonucleotides; (c) performing reverse transcription followed by PCR amplification to obtain cDNAs corresponding to the mRNA transcripts from single cells; (d) sequencing the cDNAs; and (e) identifying multiple mRNA transcripts (e.g., paired antigen receptor sequences) for a plurality of single cells based on the sequencing. For example, in some aspects, a method is provided for obtaining a plurality of paired antibody VH and VL sequences comprising (a) isolating single B-cells in individual compartments with immobilized oligonucleotides for priming of reverse transcription; (b) lysing the B-cells and allowing mRNA transcripts to associate with the immobilized oligonucleotides; (c) performing reverse transcription followed by PCR amplification to obtain cDNAs corresponding to the mRNA transcripts from single B-cells; (d) sequencing the cDNAs; and (e) identifying the paired antibody VH and VL sequences for a plurality of single B-cells. In further aspects, a method is provided for obtaining a plurality of paired T-cell receptor sequences comprising (a) isolating single T-cells in individual compartments with immobilized oligonucleotides for priming of reverse transcription; (b) lysing the T-cells and allowing mRNA transcripts to associate with the immobilized oligonucleotides; (c) performing reverse transcription followed by PCR amplification to obtain cDNAs corresponding to the mRNA transcripts from single T-cells; (d) sequencing the cDNAs; and (e) identifying the paired T-cell receptor sequences for a plurality of single T-cells based on the sequencing.

In further aspects, the method comprises obtaining sequences from at least 10,000, 100,000 or 1,000,000 individual cells (e.g., between about 100,000 and 10 million or 100 million individual cells). Thus, in some aspects, a method comprises obtaining at least 5,000, 10,000 or 100,000 individual paired antibody VH and VL sequences (e.g., between about 10,000 and 100,000, 1 million or 10 million individual paired sequences). In certain aspect, obtaining paired sequence, such as VH and VL sequences, may comprise linking cDNAs (e.g., VH and VL cDNAs) by performing overlap extension reverse transcriptase polymerase chain reaction to link cDNAs in single molecules. In an alternative aspect, a method of the embodiments does not comprise the use of overlap extension reverse transcriptase polymerase chain reaction. For example, two (or more) cDNA sequences can be obtained by sequencing of distinct molecules, such as by sequencing distinct separate VH and VL cDNA molecules.

In one aspect, the method may further comprise determining natively paired transcripts using probability analysis. In this aspect, identifying the paired transcripts may comprise comparing raw sequencing read counts. For example, a probability analysis may comprise performing the steps of FIG. 9. In a specific aspect, a method may comprise identifying the paired antibody VH and VL sequences by performing a probability analysis of the sequences. In certain aspects, the probability analysis may be based on the CDR-H3 and/or CDR-L3 sequences. In some cases, identifying the paired antibody VH and VL sequences may comprise comparing raw sequencing read counts. In a further aspect, the probability analysis may comprise performing the steps of FIG. 9.

Certain aspects of the present embodiments concern mRNA capture agents. For example, the mRNA capture agent can be a solid support, such as a bead, comprising immobilized oligonucleotides or polymer networks such as dextran and agarose. In one aspect, the bead is a silica bead or a magnetic bead. The mRNA capture agent may comprise oligonucleotides which hybridize mRNA. For example, the oligonucleotides may comprise at least one poly(T) and/or primers specific to a transcript of interest. In certain aspects, a bead of the embodiments is smaller than the individual cells that being isolated (e.g., B cells).

In some aspects, individual compartments of the embodiments may be wells in a gel or microtiter plate. In one aspect, the individual compartments may have a volume of less than 5 nL. In some aspects, the wells may be sealed with a permeable membrane prior to lysis of the cells or prior to performing RT-PCR. In yet a further aspect, the individual compartments may be microvesicles in an emulsion.

In further aspects aspect, sequestering single cells (and an mRNA capture agent) and lysis of the cells (steps (a) and (b)) may be performed concurrently. Thus, in some aspects, a method may comprise isolating single cells and an mRNA capture agents into individual microvesicles in an emulsion and in the presence of a cell lysis solution.

In further aspects, a method of the embodiments may comprise linking cDNA by performing overlap extension reverse transcriptase polymerase chain reaction to link at least 2 transcripts into a single DNA molecule (e.g., in step (e)). In alternative aspects, step (e) may not comprise the use of overlap extension reverse transcriptase polymerase chain reaction. In certain aspects, step (e) may comprise linking cDNA by performing recombination.

In yet further aspects, sequestering the single cells may comprise introducing cells to a device comprising a plurality of microwells so that the majority of cells are captured as single cells (along with an mRNA capture agent, such as a bead). In further aspects, a method may comprise sequencing of two or more transcripts covalently linked to the same bead.

Thus, in some embodiments, a method is provided for obtaining a plurality of paired antibody VH and VL sequences wherein the cells are B-cells. In one aspect, the method is a method for obtaining paired antibody VH and VL sequences for an antibody that binds to an antigen of interest. In certain aspects, the beads may be conjugated to the antigen of interest and the oligonucleotides only be conjugated to the beads in the presence of an antibody that binds to the antigen of interest. For example, beads may be coated with an antigen of interest and the mRNA capture agent (e.g., oligo-T) may associate with the bead only in the presence of an antibody that binds to the antigen (see e.g., FIG. 10). For instance, the mRNA capture agent may be associated with protein-A or otherwise functionalized to bind to an antibody if present.

Certain aspects of the embodiments may concern obtaining a sample from a subject (e.g., a sample comprising cells for use in the methods of the embodiments). Samples can be directly taken from a subject or can be obtained from a third party. Samples include, but are not limited to, serum, mucosa (e.g., saliva), lymph, urine, stool, and solid tissue samples. Similarly, certain aspects of the embodiments concern biological fluids and antibodies and/or nucleic acids therefrom. For example, the biological fluid can be blood (e.g., serum), cerebrospinal fluid, synovial fluid, maternal breast milk, umbilical cord blood, peritoneal fluid, mucosal secretions, tears, nasal, secretions, saliva, milk, or genitourinary secretions. In certain aspects, cells for use according to the embodiments are mammalian cells, such as mouse, rat or monkey cells. In preferred aspects the cells are human cells.

In some aspects, cells for use in the embodiments B cells, such as B cells from a selected organ, such as bone marrow. For example, the B cells can be mature B cells, such as bone marrow plasma cells, spleen plasma cells, or lymph node plasma cells, or cells from peripheral blood or a lymphoid organ. In certain aspects, B cells are selected or enriched based on differential expression of cell surface markers (e.g., Blimp-1, CD138, CXCR4, or CD45). In some cases, sequences of a selected class of antibodies are obtained, such as IgE, IgM, IgG, or IgA sequences.

In further aspects, a method of the embodiments may comprise immunizing the subject (e.g., prior to obtaining a cell sample). The method may further comprise isolation of a lymphoid tissue. The lymphoid tissue isolation may at least or about 1, 2, 3, 4, 5, 6, 6, 8, 9, 10 days or any intermediate ranges after immunization. The method may further comprise obtaining a population of nucleic acids of lymphoid tissue, preferably without separating B cells from the lymphoid tissue. The lymphoid tissue may be a primary, secondary, or tertiary lymphoid tissue, such as bone marrow, spleen, or lymph nodes. The subject may be any animal, such as mammal, fish, amphibian, or bird. The mammal may be human, mouse, primate, rabbit, sheep, or pig.

For determining the nucleic acid sequences (e.g., in the B cells or in lymphoid tissues), any nucleic acid sequencing methods known in the art may be used, including high-throughput DNA sequencing. Non-limiting examples of high-throughput sequencing methods comprise sequencing-by-synthesis (e.g., 454 sequencing), sequencing-by-ligation, sequencing-by-hybridization, single molecule DNA sequencing, multiplex polony sequencing, nanopore sequencing, or a combination thereof.

In a further embodiment, the present invention provides a system comprising (a) an aqueous fluid phase exit disposed within an annular flowing oil phase; and (b) an aqueous fluid phase, wherein the aqueous phase fluid comprises a suspension of cells and is dispersed within the flowing oil phase, resulting in emulsified droplets with low size dispersity comprising an aqueous suspension of cells. In one aspect, the aqueous fluid phase exit is a needle. In a further aspect, the aqueous fluid phase exit is a glass tube. In certain aspects, the oil phase flows through a glass tube or polymeric tubing. In certain aspects, the aqueous phase flows through polymeric tubing. In still a further aspect, the concentration of cells, aqueous fluid phase flow rate, and oil phase flow rate allow for the formation of droplets, wherein each droplet contains a single cell. In some aspects, the cells are selected from the group consisting of: B cells, T cells, NKT cells, and cancer cells. In certain aspects, the aqueous fluid phase comprises beads for nucleic acid capture reverse transcription reagents, polymerase chain reaction reagents, and/or combinations thereof.

In yet a further embodiment, the present invention provides a composition comprising (a) a bead; (b) an oligonucleotide capable of binding mRNA; and (c) two or more primers specific for a transcript of interest.

In still a further embodiments embodiment, the present invention provides a composition comprising an emulsion having a plurality of individual microvesicles, said microvesicles comprising a bead with immobilized oligonucleotides for priming of reverse transcription and individual B-cells, which have been disrupted to release mRNA transcripts.

In certain embodiments, the present invention provides a method comprising (a) adding a common sequence to the 5' region of two or more oligonucleotides that are specific to a set of gene targets; (b) performing nucleic acid amplification of the set of gene targets by priming the common sequence; and (c) including in the nucleic acid amplification oligonucleotides comprising the common sequence immobilized onto a surface such that immobilized oligonucleotides prime nucleic acid amplification, and resulting in surface capture of amplified sequences.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 10 schematic shows and exemplary process of mRNA capture from isolated single cells encoding high-affinity antibodies for a particular antigen. (a) Antibody-secreting B cells (top left) are isolated into compartments containing beads with immobilized antigen. Secreted antibody (gray) is captured by the beads if the B cell encodes a high-affinity antibody for the antigen. (b) Any unbound cell-secreted antibodies are washed away and an anti-IgG antibody (white) with linked poly(dT) ssDNA (black strands) is added to the compartment. The anti-IgG:poly(dT) (or other mRNA capture moiety) construct is immobilized on beads containing captured antibody. poly(dT) ssDNA is co-localized only with cells that secrete high-affinity antibody to the desired antigen. (c) The compartments are sealed and cells are lysed. mRNA strands (small circles) released from cells which secreted high-affinity antibody are captured via hybridization to the poly(dT) on poly(dT):antibody:bead constructs. Next, beads can be recovered for single-cell mRNA transcript analysis.

DESCRIPTION OF ILLUSTRATIVE EMBODIMENTS

Figure 1:
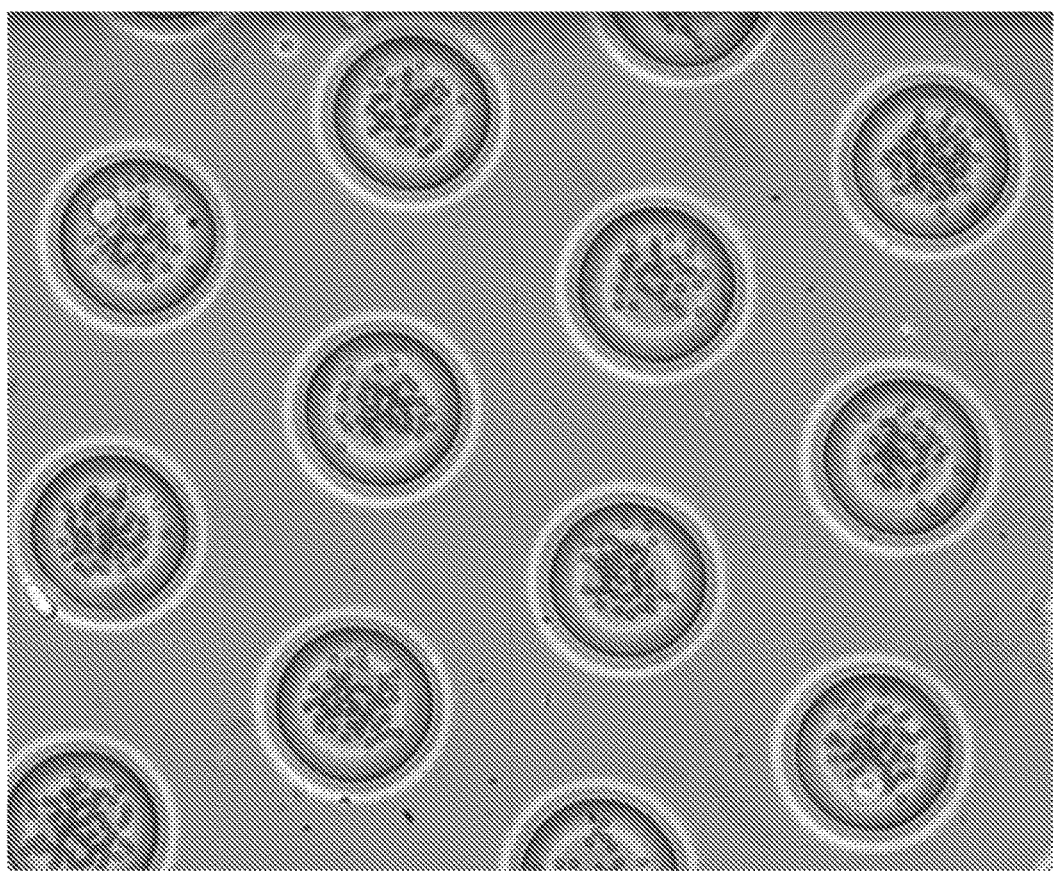
FIG. 1 shows cells isolated into individual sealed wells. The small, spherical objects within the wells are beads. This image is taken through the dialysis membrane. Well diameter is approximately 56 μm.

The present disclosure generally relates to sequencing two or more genes expressed in a single cell in a high-throughput manner. More particularly, the present disclosure provides a method for high-throughput sequencing of pairs of transcripts co-expressed in single cells to determine pairs of polypeptide chains that comprise immune receptors (e.g., antibody VH and VL sequences).

The methods of the present disclosure allow for the repertoire of immune receptors and antibodies in an individual organism or population of cells to be determined Particularly, the methods of the present disclosure may aid in determining pairs of polypeptide chains that make up immune receptors. B cells and T cells each express immune receptors; B cells express immunoglobulins, and T cells express T cell receptors (TCRs). Both types of immune receptors consist of two polypeptide chains. Immunoglobulins consist of variable heavy (VH) and variable light (VL) chains. TCRs are of two types: one consisting of an α and a β chain, and one consisting of a γ and a δ chain. Each of the polypeptides in an immune receptor has constant region and a variable region. Variable regions result from recombination and end joint rearrangement of gene fragments on the chromosome of a B or T cell. In B cells additional diversification of variable regions occurs by somatic hypermutation. Thus, the immune system has a large repertoire of receptors, and any given receptor pair expressed by a lymphocyte is encoded by a pair of separate, unique transcripts. Only by knowing the sequence of both transcripts in the pair can one study the receptor as a whole. Knowing the sequences of pairs of immune receptor chains expressed in a single cell is also essential to ascertaining the immune repertoire of a given individual or population of cells.

Currently available methods to analyze multiple transcripts in single cells, such as the two transcripts that comprise adaptive immune receptors, are limited by low throughput and very high instrumentation and reagent costs. No technology currently exists for rapidly analyzing how many cells express a set of transcripts of interest or, more specifically, for sequencing native lymphocyte receptor chain pairs at very high throughput (greater than 10,000 cells per run). The present disclosure aims to correct these deficiencies by providing a new technique for sequencing multiple transcripts simultaneously at the single-cell level with a throughput two to three orders of magnitude greater than the current state of the art.

One advantage of the methods of the present disclosure is that the methods result in a higher throughput several orders of magnitude larger than the current state of the art. In addition, the present disclosure allows for the ability to link two transcripts for large cell populations in a high throughput manner, faster and at a much lower cost than competing technologies.

In certain embodiments, the present disclosure provides methods comprising separating single cells in a compartment with beads conjugated to oligonucleotides; lysing the cells; allowing mRNA transcripts released from the cells to hybridize with the oligonucleotides; performing overlap extension reverse transcriptase polymerase chain reaction to covalently link DNA from at least two transcripts derived from a single cell; and sequencing the linked DNA. In certain embodiments, the cells may be mammalian cells. In certain embodiments, the cells may be B cells, T cells, NKT cells, or cancer cells.

In other embodiments, the present disclosure provides methods comprising separating single cells in a compartment with beads conjugated to oligonucleotides; lysing the cell; allowing mRNA transcripts released from the cells to hybridize with the oligonucleotides conjugated to the beads; performing reverse transcriptase polymerase chain reaction to form at least two cDNAs from at least two transcripts derived from a single cell; and sequencing the cDNA attached to the beads.

In another embodiment, the present disclosure provides a method comprising mixing cells with beads having a diameter smaller than the diameter of the cells, wherein the beads are conjugated to oligonucleotides, sequestering the cells and beads within compartments having a volume of less than 5 nL, lysing the cells and allowing mRNA transcripts to associate with the beads, isolating the beads and associated mRNA from the compartments, performing reverse transcription followed by PCR amplification on the bead-associated mRNA, and sequencing the DNA product from each bead to identify cDNA associated with each bead.

In other embodiments, the present disclosure provides a system comprising an aqueous fluid phase exit disposed within an annular flowing oil phase, wherein the aqueous phase fluid comprises a suspension of cells and is dispersed within the flowing oil phase, resulting in emulsified droplets with low size dispersity comprising an aqueous suspension of cells.

In other embodiments, the present disclosure provides a composition comprising a bead, an oligonucleotide capable of binding mRNA, and two or more primers specific for a transcript of interest.

Figure 6:
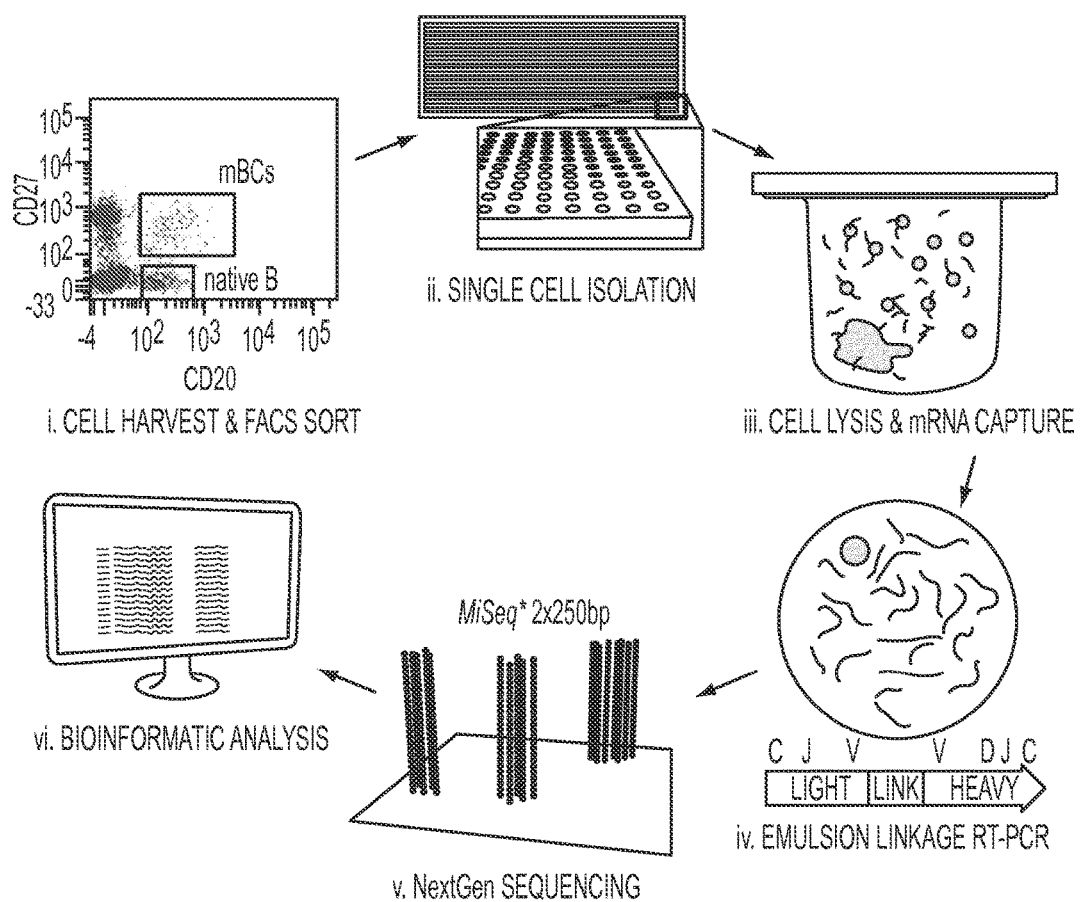
FIG. 6 presents an overview of high-throughput sequencing technology for multiple transcripts applied toward the sequencing of native antibody VH and VL mRNAs from B-cell populations. i) B-cell populations are sorted for desired phenotype (e.g., mBCs, memory B cells, naive BCs, naive B cells). ii) Single cells are isolated by random settling into a microwell array; poly(dT) microbeads are also added to the wells. iii) Wells are sealed with a dialysis membrane and equilibrated with lysis buffer to lyse cells and anneal VH and VL mRNAs to poly(dT) beads (blob represents a lysed cell, circles depict magnetic beads, black lines depict mRNA strands). iv) Beads are recovered and emulsified for cDNA synthesis and linkage PCR to generate an ~850-base pair VH:VL cDNA product. v) Next-generation sequencing is performed to sequence the linked strands. vi) Bioinformatic processing is used to analyze the paired VH:VL repertoire.

In certain embodiments, the present disclosure also provides for a device comprising ordered arrays of microwells, each with dimensions designed to accommodate a single lymphocyte cell. In one embodiment, the microwells may be circular wells 56 μm in diameter and 50 μm deep, for a total volume of 125 pL. Such microwells would normally range in volume from 20-3,000 pL, though a wide variety of well sizes, shapes and dimensions may be used for single cell accommodation. In certain embodiments, the microwell may be a nanowell. In certain embodiments, the device may be a chip. The device of the present disclosure allows the direct entrapment of tens of thousands of single cells, with each cell in its own microwell, in a single chip. In certain embodiments, the chip may be the size of a microscope slide. In one embodiment, a microwell chip may be used to capture single cells in their own individual microwells (FIG. 6). The microwell chip can be made from polydimethylsiloxane (PDMS); however, other suitable materials known in the art such as polyacrylimide, silicon and etched glass may also be used to create the microwell chip.

Several beads or other particles conjugated with oligonucleotides may also be captured in the microwells with the single cells according to the methods of the present disclosure. In certain embodiments, beads may comprise oligonucleotides immobilized on the surface of the beads. In other embodiments, the beads may be magnetic. In other embodiments, the beads may be coated with one or more oligonucleotides. In certain embodiments, the oligonucleotides may be a poly(T), a sequence specific for heavy chain amplification, and/or a sequence specific for light chain amplification. A dialysis membrane covers the microwells, keeping the cells and beads in the microwells while lysis reagents are dialyzed into the microwells. The lysis reagents cause the release of the cells' mRNA transcripts into the microwell with the beads. In embodiments where the oligonucleotide is poly(T), the poly(A) mRNA tails are captured by the poly(T) oligonucleotides on the beads. Thus, each bead is coated with mRNA molecules from a single cell. The beads are then pooled, washed, and resuspended in solution with reagents for overlap extension (OE) reverse transcriptase polymerase chain reaction (RT-PCR). This reaction mix includes primers designed to create a single PCR product comprising cDNA of two transcripts of interest covalently linked together. Before thermocycling, the reagent solution/bead suspension is emulsified in oil phase to create droplets with no more than one bead per droplet. The linked cDNA products of OE RT-PCR are recovered and used as a template for nested PCR, which amplifies the linked transcripts of interest. The purified products of nested PCR are then sequenced and pairing information is analyzed (FIG. 6). In other embodiments, restriction and ligation may be used to link cDNA of multiple transcripts of interest. In other embodiments, recombination may be used to link cDNA of multiple transcripts of interest.

The present disclosure also provides a method to trap mRNA from single cells on beads, perform cDNA synthesis, link the sequences of two or more desired cDNAs from single cells to create a single molecule, and finally reveal the sequence of the linked transcripts by High Throughput (Next-gen) sequencing. According to the present disclosure, one way to increase throughput in biological assays is to use an emulsion that generates a high number of 3-dimensional parallelized microreactors. Emulsion protocols in molecular biology often yield 109-1011 droplets per mL (sub-pL volume). Emulsion-based methods for single-cell polymerase chain reaction (PCR) have found a wide acceptance, and emulsion PCR is a robust and reliable procedure found in many next-generating sequencing protocols. However, very high throughput RT-PCR in emulsion droplets has not yet been implemented because cell lysates within the droplet inhibit the reverse transcriptase reaction. Cell lysate inhibition of RT-PCR can be mitigated by dilution to a suitable volume.

In another embodiment, cells are lysed in emulsion droplets containing beads for nucleic acid capture. In certain embodiments, the beads may be conjugated with oligonucleotide. In certain embodiments, the oligonucleotide may be poly(T). In other embodiments, the oligonucleotide may be a primer specific to a transcript of interest. In certain embodiments, the bead may be magnetic. An aqueous solution with a suspension of both cells and beads is emulsified into oil phase by injecting an aqueous cell/bead suspension into a fast-moving stream of oil phase. The shear forces generated by the moving oil phase create droplets as the aqueous suspension is injected into the stream, creating an emulsion with a low dispersity of droplet sizes. Each cell is in its own droplet along with several beads conjugated with oligonucleotides. The uniformity of droplet size helps to ensure that individual droplets do not contain more than one cell. Cells are then thermally lysed, and the mixture is cooled to allow the beads to capture mRNA. The emulsion is broken and the beads are collected. The beads are resuspended in a solution for emulsion OE RT-PCR to link the cDNAs of transcripts of interest together. Nested PCR and sequencing of the linked transcripts is performed according to the present disclosure. In certain embodiments, the aqueous suspension of cells comprises reverse transcription reagents. In certain other embodiments, the aqueous suspension of cells comprises at least one of polymerase chain reaction and reverse transcriptase polymerase chain reaction reagents. In other embodiments, restriction and ligation may be used to link cDNA of multiple transcripts of interest. In other embodiments, recombination may be used to link cDNA of multiple transcripts of interest.

In another embodiment, emulsion droplets which contain individual cells and RT-PCR reagents are formed by injection into a fast-moving oil phase. Thermal cycling is then performed on these droplets directly. In certain embodiments, an overlap extension reverse transcription polymerase chain reaction may be used to link cDNA of multiple transcripts of interest.

In another embodiment, cDNAs of interest from a single cell are attached via RT-PCR to beads as described below, and the transcripts on the beads are sequenced directly using high-throughput sequencing. An equal mixture of three species of functionalized oligonucleotide primers may be conjugated to functionalized beads. One of the oligonucleotides may be poly(T) to capture the poly(A) tail of mRNAs. The other two oligonucleotides may be specific primers for amplifying the transcripts of interest. Beads prepared in this way are mixed with cells in an aqueous solution, and the cell/bead suspension is emulsified so that each cell is in its own droplet along with an excess of beads. In certain embodiments an average of 55 beads may be contained in each droplet. Cells are thermally lysed, and poly(T) oligonucleotides on the beads bind mRNAs. The emulsion is broken, and beads are collected, washed, and resuspended in a solution with reagents and primers for RT-PCR that will result in amplification of the transcripts of interest in such a way that the transcripts are attached to the beads. The bead suspension is emulsified and RT-PCR is performed. The beads are collected and submitted for high-throughput sequencing, which directly sequences the two transcripts attached to the beads by initiating multiple sequence reads using at least two different primers, where each initiation primer is specific to a transcript of interest. The two transcripts are paired by bead location in the high-throughput sequencing grid, revealing sequences that are expressed together from a single cell. Sequencing can be performed, for example, on Applied Biosystem's SOLiD platform, Life Technologies' Proton Torrent, or Illumina's HiSeq sequencing platform.

Primer design for OE RT-PCR determines which transcripts of interest expressed by a given cell are linked together. For example, in certain embodiments, primers can be designed that cause the respective cDNAs from the VH and VL chain transcripts to be covalently linked together. Sequencing of the linked cDNAs reveals the VH and VL sequence pairs expressed by single cells. In other embodiments, primer sets can also be designed so that sequences of TCR pairs expressed in individual cells can be ascertained or so that it can be determined whether a population of cells co-expresses any two genes of interest.

Bias can be a significant issue in PCR reactions that use multiple amplification primers because small differences in primer efficiency generate large product disparities due to the exponential nature of PCR. One way to alleviate primer bias is by amplifying multiple genes with the same primer, which is normally not possible with a multiplex primer set. By including a common amplification region to the 5' end of multiple unique primers of interest, the common amplification region is thereby added to the 5' end of all PCR products during the first duplication event. Following the initial duplication event, amplification is achieved by priming only at the common region to reduce primer bias and allow the final PCR product distribution to remain representative of the original template distribution.

Such a common region can be exploited in various ways. One clear application is to add the common amplification primer at higher concentration and the unique primers (with 5' common region) at a low concentration, such that the majority of nucleic acid amplification occurs via the common sequence for reduced amplification bias. Another application is the surface-based capture of amplification products, for example to capture PCR product onto a microbead during emulsion PCR. If the common sequence oligonucleotides are immobilized onto a bead surface, the PCR products of interest will become covalently linked to the bead during amplification. In this way, a widely diverse set of transcripts can be captured onto a surface using a single immobilized oligonucleotide sequence.

For example, two different common regions may be immobilized onto a bead surface at equal concentration (e.g., one common sequence for heavy chain, and a different common sequence for light chain). Following PCR amplification, the bead will be coated with approximately 50% heavy chain amplification product, and 50% light chain amplification product. This balance between heavy and light chain representation on the bead surface helps ensure sufficient signal from both heavy and light chains when the bead is submitted to high throughput sequencing.

Accordingly, in certain embodiments, the present disclosure provides methods comprising adding a common sequence to the 5' region of two or more oligonucleotides that are specific to a set of gene targets; and performing nucleic acid amplification of the set of gene targets by priming the common sequence. In certain embodiments, the common sequence n is immobilized onto a surface. In other embodiments, the common sequence may be used to capture amplification products.

The methods of the present disclosure allow for information regarding multiple transcripts expressed from a single cell to be obtained. In certain embodiments, probabilistic analyses may be used to identify native pairs with read counts or frequencies above non-native pair read counts or frequencies. The information may be used, for example, in studying gene co-expression patterns in different populations of cancer cells. In certain embodiments, therapies may be tailored based on the expression information obtained using the methods of the present disclosure. Other embodiments may focus on discovery of new lymphocyte receptors.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of a High Density Microwell Plate

A grid of micropillars (56 µm diameter, 50 µm height) are photolithographically patterned onto a silica wafer using SU-8 photoresist (Fisher Scientific) and the silica wafer is used as a mold to print polydimethylsiloxane (PDMS) chips (Sylgard 184, Dow Corning) with the dimensions of a standard microscope slide and containing approximately 170,000 wells per chip. Dimensions of the micropillar may range from about 5 µm to about 300 µm wide and from about 5 µm to about 300 µm high. Molded PDMS chips are silanized in an oxygen plasma chamber for 5 minutes to generate a hydrophilic surface. The PDMS chips are then blocked in 1% bovine serum albumin (BSA) for 30 minutes and washed in deionized water and phosphate-buffered saline (PBS) to prepare for cell seeding.

Example 2

Method for Linking Two Transcripts from a Single Cell in a High Throughput Manner The process for physically linking two or more transcripts derived from a single cell in a high throughput manner uses the sealed PDMS microwell device of Example 1 to trap single cells into separate wells. Cell lysis also occurs, and poly(T) magnetic micron size beads for mRNA capture are also introduced into the microwells. Once cells and beads have been loaded, the device is sealed with dialysis membrane and a lysis solution is introduced. Subsequently, beads are recovered, resuspended in solution with reagents, primers and polymerase enzyme for overlap extension (OE) RT-PCR, and the solution is then emulsified so that each bead is encapsulated within a single emulsion droplet. The emulsion is subjected to thermal cycling to physically link the two transcripts (e.g., immunoglobulin heavy and light chain cDNA), and the linked products are recovered from the emulsion following cycling. A nested PCR amplification is performed, and then the resulting DNA is sequenced using Illumina or any other NextGen sequencing technology that can yield reads of appropriate length to unequivocally interpret the transcript pairing information (FIG. 6).

The method outlined above was employed to link the immunoglobulin variable heavy (VH) and variable light (VL) chains in mixtures comprising the mouse hybridoma cell lines MOPC-21 and MOPC-315. The VH and VL sequences expressed by each of these cell lines is known and hence these experiments served for method validation. 5 mL each of MOPC-21 and MOPC-315 cells were separately withdrawn from culture two days after passage (cells were grown in Falcon vented T-25 culture flasks, 10 mL volume in RPMI-1640, 10% FBS, 1% P/S) and placed in 15 mL tubes. Cell density of 150,000 viable cells/mL with >98% viability, as measured with a hemocytometer and trypan blue exclusion, were determined RNAse A was added to each tube at a concentration of 30 µg/mL and cells were incubated at 37° C. for 30 minutes. Then, cells were washed three times with complete culture media and twice with PBS (pH 7.4). Washes were accomplished by centrifugation at 250 g at room temperature for 5 minutes followed by aspiration and resuspension. Cell concentrations were counted again with a hemocytometer, and MOPC-21 and MOPC-315 cells were mixed to form a cell suspension with a total concentration of 35,000 cells/mL in PBS, composed of 17,500 MOPC-21 cells/mL and 17,500 MOPC-315 cells/mL.

500 µL of the MOPC-21 and MOPC-315 cell mixture were applied to a PDMS microwell device that had been incubated with BSA to block non-specific adsorption. 17,500 total cells were added to each chip. Four chips were used in parallel (70,000 total cells distributed across four PDMS chips), and cells were allowed to settle into wells by gravity over the course of 5 minutes with gentle agitation. As each PDMS chip contains approximately 120,000 wells and cell loading efficiently is estimated at approximately 70%, approximately 1 in 10 wells contain isolated cells. The incidence of two cells per well can be accurately estimated with Poisson statistics, and under these conditions, >95% of wells containing cells contained a single cell.

The surfaces of the microwell devices were then washed with PBS to remove unadsorbed cells from the chip surfaces, and 25 µL of poly(T) magnetic beads (mRNA Direct Kit, 2.8 µm diameter, Invitrogen Corp.) was resuspended in 50 µL PBS and applied to each microwell device surface, for an average of 55 poly(T) beads per well. After magnetic beads were allowed to settle into wells by gravity, a BSA-blocked dialysis membrane (12,000-14,000 MWCO regenerated cellulose, 25 mm flat width, Fisher Scientific) that had been rinsed in PBS was laid over each chip surface. PBS was removed from the chip and membrane surfaces using a 200 µL pipette. Then, the tapered end of a 1000 µL pipette tip was cut to form a flat cylinder that was dragged across the membranes, pressing the membranes to the PDMS chips and eliminating excess PBS from between the PDMS microwell devices and dialysis membrane, which sealed the microwells and trapped cells and beads inside (FIG. 1).

Figure 2:
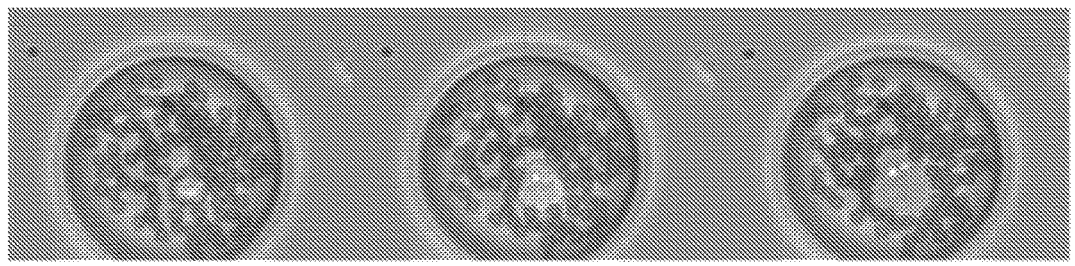
FIG. 2 shows Left: An isolated single cell immediately prior to lysis; Center: The cell in the process of lysing; and Right: The microwell immediately after lysis, using time-lapse microscopy. Well diameter is approximately 56 μm.

Cell lysis and mRNA binding to the poly(T) magnetic beads trapped within microwells was accomplished by dialysis. 500 µL of cell lysis solution (500 mM LiCl in 100 mM tris buffer (pH 7.5) with 0.1% sodium deoxycholate and 10 mM ribonucleoside vanadyl complex) was applied to the dialysis membranes, and lysis occurred at room temperature as reagents dialyzed into microwells. Cell lysis was fully complete in <5 minutes as determined by time-lapse microscopy (FIG. 2).

Figure 3:
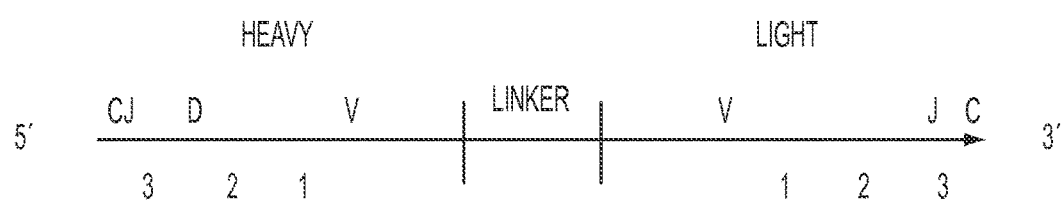
FIG. 3 shows linked OE RT-PCR product. Letters indicate approximate locations of constant, variable, joining, and diversity regions, while numbers indicate approximate locations of complementarity-determining regions.

PDMS microwell chips were maintained for 20 minutes at room temperature inside a Petri dish, then placed in a cold room at 4° C. for 10 additional minutes. A Dynal MPC-S magnet was placed underneath the PDMS microwell device to hold magnetic beads inside microwells as the dialysis membrane was removed with forceps and discarded. The magnet was then placed underneath another Petri dish with 4 subdivisions, one of which contained 2 mL of cold mRNA Direct Lysis/Binding Buffer (100 mM tris pH 7.5, 500 mM LiCl, 10 mM EDTA, 1% LiDS, 5 mM DTT). The four PDMS microwell devices were sequentially inverted and resuspended in the 2 mL of solution to allow the magnet to draw beads out of microwells and into the mRNA Direct Lysis/Binding buffer solution. Magnetic beads were then resuspended in the 2 mL mRNA Direct Lysis/Binding Buffer and the solution was divided into two Eppendorf tubes and placed on the Dynal MPC-S magnetic rack. Beads were washed once without resuspension using 1 mL per tube of Wash Buffer 1 (100 mM tris pH 7.5, 500 mM LiCl, 1 mM EDTA, 4° C.). Beads were then immediately washed again in Wash Buffer 1 with resuspension. Beads were then immediately resuspended in Wash Buffer 2 (20 mM tris pH 7.5, 50 mM KCl, 3 mM MgCl) and replaced on the magnetic rack. Finally, beads were suspended in 2.85 mL cold RT-PCR mixture (Quanta OneStep Fast, VWR) containing 0.05 wt % BSA (Invitrogen Ultrapure BSA, 50 mg/mL) and primer concentrations listed in Table 1. Amplification was accomplished with two common primers (CHrev-AHX89 and CLrev-BRH06) at high concentration which anneal to the reverse complement of the 5' end of CLrev and CHrev specific primers. V-region primers also contain linker sequences at the 5' end to effect VH-VL linkage. 25 µL of cold the RT-PCR mixture was previously reserved for cycling without beads or emulsification as a non-template control. The cold RT-PCR mixture containing the poly(T) magnetic beads was added dropwise to a stirring Ika dispersing tube (DT-20, VWR) containing 9 mL chilled oil phase (molecular biology grade mineral oil with 4.5% Span-80, 0.4% Tween 80, 0.05% Triton X-100, v/v % oil phase reagents from Sigma Aldrich Corp.), and the mixture was agitated for 5 minutes at low speed. The resulting emulsion was added to 96-well PCR plates, with 100 µL emulsion per well, and placed in a thermocycler. The RT step was performed under the following conditions: 30 minutes at 55° C., followed by 2 min at 95° C. PCR amplification was then performed under the following conditions: three cycles of 94° C. for 30 s denature, 57° C. for 1 min anneal, and 72° C. for 3 min extend; then twenty-seven cycles of 94° C. for 30 s denature, 59° C. for 30 s anneal, and 72° C. for 3 min extend; then a final extension step for 7 min at 72° C. FIG. 3 shows a diagram of the final linked products.

TABLE 1

Primers for MOPC-21/MOPC-315 emulsion linkage RT-PCR.

| Conc. | Primer ID |
|---|---|
| 400 | CLrev-BRH06 |
| 400 | CHrev-AHX89 |
| 40 | MOPC21-CHrev-AHX89 |
| 40 | MOPC21-CLrev-BRH06 |
| 40 | MOPC315-CLrev-BRH06 |
| 40 | MOPC315-CHrev-AHX89 |
| 40 | MOPC21-VH-OE2 |
| 40 | MOPC21-VL-OE2 |
| 40 | MOPC315-VH-OE |
| 40 | MOPC315-VL-OE |

Following thermal cycling, the emulsion was collected and divided into three Eppendorf tubes and centrifuged at room temperature for 10 minutes at 16,000 g. The mineral oil upper phase was discarded, and 1.5 mL diethyl ether was added to extract the remaining oil phase and break the emulsion. The upper ether layer was removed and two more ether extractions were performed. Then the ether layer was discarded, and residual ether solvent was removed in a SpeedVac for 25 minutes at room temperature. The remaining aqueous phase was diluted 5:1 in DNA binding buffer, then split in three parts and passed through three silica spin columns (DNA Clean & Concentrator, Zymo Research Corp.) to capture the RT-PCR cDNA product. After washing each column with 300 µL wash buffer (Zymo Research Corp), cDNA was eluted with 20 µL in each column, and a nested PCR reaction was performed (ThermoPol PCR buffer with Taq Polymerase, New England Biosciences) in a total volume of 200 µL using 4 µL eluted cDNA as template. After a 2 min denaturing step at 94° C., cycling was performed at 94° C. for 30 s denature, 62° C. for 30 s anneal, 72° C. for 20 s extend, for 30 cycles. 400 nM of each nested primer (Table 2) was used to amplify linked heavy and light chains, which generated an approximately 800 bp linked product.

TABLE 2

Primers for MOPC-21/MOPC-315 nested PCR.

| Conc. | Primer ID |
|---|---|
| 400 | MOPC21-CHrev-seq |
| 400 | MOPC21-CLrev-seq |
| 400 | MOPC315-CHrev-seq |

TABLE 2-continued

Primers for MOPC-21/MOPC-315 nested PCR.

| Conc. | Primer ID |
|---|---|
| 400 | MOPC315-CLrev-seq |

Nested PCR product was electrophoresed on a 1% agarose gel, and the 800 bp band was excised and dissolved in agarose-dissolving buffer for 10 minutes at 50° C., then captured onto and eluted from a silica spin column according to manufacturer protocols (Zymo Research Corp.) to obtain purified nested PCR product. Purified cDNA was submitted for base pair paired-end reads with the Illumina HiSeq sequencing platform. Other NextGen sequencing technology (e.g. Roched 454, Pacific Biosciences etc.) capable of providing reads suitable for identifying the linked transcript can also be used for this purpose. (FIG. 3). HiSeq data output was mapped to known MOPC-21 and MOPC-315 sequences using the SHort Read Mapping Package software (SHRiMP) and filtered for high-quality reads with >90% identity to known transcript sequences. In this manner, approximately 18,000 linked heavy and light chain sequences were obtained (Table 3).

TABLE 3

Raw read counts for sequenced VH-VL pairs.

| | | Light | |
|---|---|---|---|
| | | MOPC-21 | MOPC-315 |
| Heavy | MOPC-21 | 9,689 | 426 |
| | MOPC-315 | 1,042 | 6,591 |

Correct transcript pairings were further determined from the degree of pairing skewness of the raw DNA sequencing data. For any given two transcripts, e.g., immunoglobulin heavy chain $H_i$ and light chain $L_j$, with overall heavy or light chain mapped frequencies $f_{Hi}$ and $f_{Lj}$, a measure of pairing skewness, s, is computed:

$$s = \frac{\text{Observed reads}}{\text{Expected reads(random pairing)}} = \frac{[(\# \ Hi)]Lj \text{ pairs})]}{fHi \times fLj \times (\# \text{ total pairs})}$$

The calculated value s compares VL frequency paired with a particular VH to the VL frequency in the entire sequence set. A value of s>1 indicates that a heavy-light pair is observed at a frequency above that corresponding to random pairing. Natural pairings are deduced from entries with a maximum value of s (Table 4). Pairing skewness, s, for sequenced heavy and light pairs, calculated from approximately 18,000 sequenced VH-VL linked pairs are is shown in Table 4. Native heavy-light pairings are predicted by the maximal value of s for each heavy chain and are highlighted in green. This table demonstrates the capacity of our method to resolve native heavy and light chain pairings from a heterogeneous mixture of cells.

TABLE 4

Calculated Pairing Skewness.

| | | Light | |
|---|---|---|---|
| | | MOPC-21 | MOPC-315 |
| Heavy | MOPC-21 | 1.58 | 0.11 |
| | MOPC-315 | 0.23 | 2.18 |

Example 3

High-Throughput Transcripts Pairing Analysis Using Defined Mixtures of 5 Cell Lines Five immortalized B cell lines were mixed at different ratios and used to examine pairing efficiency of the linked products generated by OE-PCR. The five B cell lines used in this experiment were: MOPC-21, MOPC-315, IM-9, ARH-77, and DB (see Table 5). DB expresses extremely low levels of VH and VL transcript and was used as a negative control.

All cell lines were obtained from ATCC and cultured in RPMI-1640 supplemented with 10% FBS and 1% penicillin/streptomycin (see Example 2). Following a 30-minute RNAse treatment and subsequent wash, cells were seeded into microwells at a density of 17,500 total cells per chip along with poly(T) magnetic beads according to Example 2. Wells were sealed with a dialysis membrane, cells were lysed, and mRNA was allowed to anneal to the beads (Example 2). Beads were then recovered, resuspended in OE RT-PCR mix, and placed in an emulsion (Example 2). OE RT-PCR primer concentrations used are given in Table 6, and thermal cycling conditions are presented in Table 7.

TABLE 5

An overview of the 5 cell lines.

| % in Mix | Cell Line | ATCC ID | Organism | Ig Class | Relative Ig Expression |
|---|---|---|---|---|---|
| 65 | IM-9 | CCL-159 | Homo sapiens | IgG/IgK | Low |
| 35 | MOPC-21 | 63035 | Mus musculus | IgG/IgK | Medium |
| 6 | ARH-77 | CRL-1621 | Homo sapiens | IgG/IgK | High |
| 3 | MOPC-315 | TIB-23 | Mus musculus | IgA/IgL | Medium |
| 1 | DB | CRL-2289 | Homo sapiens | IgG/IgL | Very Low |

TABLE 6

OE RT-PCR primers for the mix of cell lines.

| Conc. | Primer ID |
|---|---|
| 400 | CLrev-BRH06 |
| 400 | CHrev-AHX89 |
| 40 | MOPC21-CHrev-AHX89 |
| 40 | MOPC21-CLrev-BRH06 |
| 40 | MOPC315-CLrev-BRH06 |

TABLE 6-continued

OE RT-PCR primers for the mix of cell lines.

| Conc. | Primer ID |
|---|---|
| 40 | MOPC315-CHrev-AHX89 |
| 40 | MOPC21-VH-OE2 |
| 40 | MOPC21-VL-OE2 |
| 40 | MOPC315-VH-OE |
| 40 | MOPC315-VL-OE |
| 40 | hIgG-rev-OE-AHX89 |
| 40 | hIgKC-rev-OE-BRH06 |
| 40 | hIgLC-rev-OE-BRH06 |
| 40 | hVH1-fwd-OE |
| 40 | hVH157-fwd-OE |
| 40 | hVH2-fwd-OE |
| 40 | hVH3-fwd-OE |
| 40 | hVH4-fwd-OE |
| 40 | hVH4-DP63-fwd-OE |
| 40 | hVH6-fwd-OE |
| 40 | hVH3N-fwd-OE |
| 40 | hVK1-fwd-OE |
| 40 | hVK2-fwd-OE |
| 40 | hVK3-fwd-OE |
| 40 | hVK5-fwd-OE |
| 40 | hVL1-fwd-OE |
| 40 | hVL1459-fwd-OE |
| 40 | hVL15910-fwd-OE |
| 40 | hVL2-fwd-OE |
| 40 | hVL3-fwd-OE |
| 40 | hVL-DPL16-fwd-OE |
| 40 | hVL3-38-fwd-OE |
| 40 | hVL6-fwd-OE |
| 40 | hVL78-fwd-OE |

TABLE 7

OE RT-PCR thermal cycling conditions.

| # Cycles | Temp (° C.) | Time (min) |
|---|---|---|
| 1 | 55 | 30 |
|  | 94 | 2 |
| 4 | 94 | 0.5 |
|  | 50 | 0.5 |
|  | 72 | 3 |
| 4 | 94 | 0.5 |
|  | 55 | 0.5 |
|  | 72 | 3 |
| 22 | 94 | 0.5 |
|  | 60 | 0.5 |
|  | 72 | 3 |
| 1 | 72 | 7 |

Emulsion OE RT-PCR product was recovered by diethyl ether extraction followed by capture on and elution from a silica spin column (Example 2) for use as template in a nested PCR under the following conditions: 94° C. for 2 min initial denature, 94° C. for 30 s denature, 62° C. for 30 s anneal, 72° C. for 20 s extend, 40 total cycles. Nested primer sequences and concentrations are reported in Tables 2 and 8.

TABLE 8

Nested PCR primers to generate approximately 800 bp linked products.

| Conc. (nM) | Primer ID |
|---|---|
| 400 | hIgG-all-rev-OEnested |
| 400 | hIgKC-rev-OEnested |
| 400 | hIgLC-rev-OEnested |

Nested PCR product was electrophoresed on a 1% agarose gel, and a region from 650 to 1000 bp was excised and purified with a silica spin column (Example 2). Recovered cDNA was submitted for Illumina HiSeq 100 bp paired-end sequencing. HiSeq data was mapped to a reference file containing heavy and light chain sequences for all five clones, and data was filtered to obtain paired-end reads with >90% match to reference sequences, as in Example 2. Natural pairings were identified by interrogating skewness of pairing data. For any given immunoglobulin heavy chain Hi and light chain Lj, with overall heavy or light chain mapped frequencies fHi and fLj, a measure of pairing skewness, s, was computed:

$$s = \frac{\text{Observed reads}}{\text{Expected reads(random pairing)}} = \frac{(\# \; Hi \; Lj \; \text{pairs})}{fHi \times fLj \times (\# \; \text{total pairs})}$$

The calculated value s compares VL frequency paired with a particular VH to the VL frequency in the entire sequence set. A value of s>1 indicates that a heavy-light pair is observed at a frequency above that corresponding to random pairing. Natural pairings are deduced from entries with a maximum value of s for each heavy chain. Table 9 shows the natural pairings identified and pairing skewness, s, for sequenced heavy and light pairs, calculated from approximately 66,000 sequenced VH-VL linked pairs. Native heavy-light pairings were predicted by the maximal value of s for each heavy chain. Table 9 demonstrates the ability of our method to resolve native heavy and light chain pairings from a heterogeneous mixture of cells with high throughput.

TABLE 9

Resolution of native heavy and light chain pairings.

| | | Light | | | |
|---|---|---|---|---|---|
| | | IM-9 | MOPC-21 | ARH-77 | MOPC-315 |
| Heavy | IM-9 | 9.11 | 0.29 | 0.48 | 0.00 |
| | MOPC-21 | 0.87 | 1.48 | 0.38 | 0.93 |
| | ARH-77 | 0.86 | 0.08 | 2.25 | 0.21 |
| | MOPC-315 | 1.91 | 0.17 | 1.89 | 23.84 |

Example 4

Method for Linking Two Transcripts from Single B Cells Trapped within High Density Microwell Plates A population of B cells is allowed to settle by gravity into PDMS microwell plates, constructed as described in Example 1. In this example, each PDMS slide contains $1.7 \times 10^5$ wells so that four slides processed concurrently accommodate 68,000 lymphocytes at a ≥1:10 cell/well occupancy, which gives at least a 95% probability of there being only one cell per well based on Poisson statistics. Poly(dT) magnetic beads with a diameter of 2.8 μm are deposited into the microwells at an average of 55 beads/well and the slides are covered with a dialysis membrane. Subsequently, the membrane-covered slides are incubated with an optimized cell lysis solution containing 1% lithium dodecyl sulfate that results in complete cell lysis within <1 min. mRNA anneals to the poly(dT) magnetic beads which are collected, washed and resuspended in solution with reagents, primers, reverse transcriptase enzyme, and polymerase enzyme for overlap extension (OE) RT-PCR. In this manner beads become isolated within the droplets that comprise the water in oil emulsion. The emulsion is subjected to thermal cycling to physically link the two transcripts (e.g. immunoglobulin heavy and light chain cDNA), and the linked products are recovered from the emulsion following cycling. A nested PCR amplification is performed, and then the resulting DNA is sequenced using Illumina or any other NextGen sequencing technology that can yield reads of appropriate length to unequivocally interpret the transcript pairing information. An overview of the process is presented in FIG. 6.

The method outlined above was employed to link the immunoglobulin variable heavy (VH) and variable light (VL) chains in mixtures of human primary cells.

A healthy 30-year-old male was vaccinated with the 2010-2011 trivalent FluVirin influenza vaccine (Novartis) and blood was drawn at day 14 after vaccination after informed consent had been obtained. PBMCs were isolated and resuspended in DMSO/10% FCS for cryopreservation. Frozen PBMCs were thawed and cell suspensions were stained in PBS/0.2% BSA with anti-human CD19 (HIB19, BioLegend, San Diego, Calif.), CD27 (O323, BioLegend), CD38 (HIT2, BioLegend) and CD3 (7D6, Invitrogen, Grand Island, N.Y.). $CD19^+CD3^-CD27^+CD38^{int}$ memory B cells were sorted using a FACSAria II sorter system (BD Biosciences, San Diego, Calif.). Cells were either cryopreserved in DMSO/10% FCS for subsequent high-throughput VH:VL pairing or single-cell sorted into 96-well plates containing RNAse Inhibitor Cocktail (Promega, Madison, Wis.) and 10 mM Tris-HCl pH 8.0 for single-cell RT-PCR analysis. cDNA was synthesized from single-sorted cells using the Maxima First Strand cDNA Synthesis Kit (Fermentas, Waltham, Mass.) followed by amplification of the immunoglobulin variable genes using primer sets and PCR conditions previously described (Smith et al., 2009). Variable genes were determined with in-house analysis software using the IMGT search engine (Brochet et al., 2008).

Figure 4:
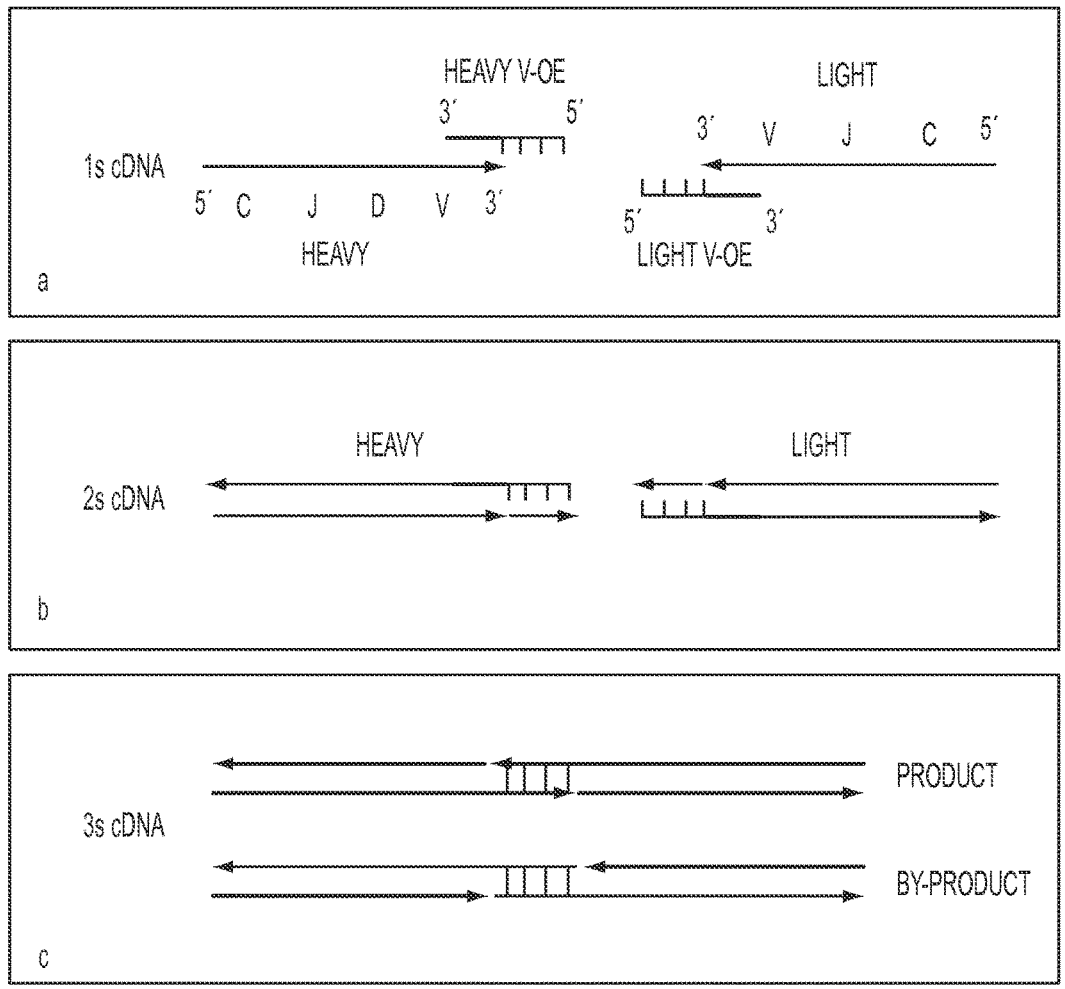
FIG. 4 shows an overview of the linkage (overlap extension) RT-PCR process. a) V-region primers with a 5' complementary heavy/light overlap region anneal to first strand cDNA. b) Second strand cDNA is formed by 5' to 3' extension; the overlap region is incorporated into all cDNA. c) After denaturation, heavy and light chains with first strand sense anneal to generate a complete 850 bp product through 5' to 3' extension. The CDR-H3 and CDR-L3 are located near the outside of the final linked construct, which allows CDR3 analysis by 2×250 paired-end Illumina sequencing.

Memory B cells frozen for high-throughput VH:VL pairing were thawed and recovered by centrifugation at 250 g for 10 min. Cells were resuspended in 200 μl RPMI-1640 supplemented with 1×GlutaMAX, 1×non-essential amino acids, 1×sodium pyruvate and 1×penicillin/streptomycin (Life Technologies) and incubated at 37° C. for 13 h in a 96-well plate. Recovered cells were centrifuged again at 250 g for 10 min and resuspended in 400 μl PBS, and 6 μl were withdrawn for cell counting with a hemocytometer. Approximately 8,800 cells were recovered from frozen stock. Memory B cells were then spiked with ~880 IM-9 cells (ATCC number CCL-159) as an internal control. Cells were resuspended over two PDMS microwell slides (340,000 wells) and allowed to settle into wells by gravity over the course of 5 min with gentle agitation. The cell seeding process has been calculated to be 90% efficient by measuring cell concentration in seeding buffers both pre- and post-cell seeding; thus 8,000 primary cells were analyzed in this experiment. The fraction of cells isolated in the single and multiple cell per well states was calculated using Poisson statistics:

$$P(k, \mu) = \frac{\mu^k e^{-\mu}}{k!}$$

where k equals the number of cells in a single microwell and μ is the average number of cells per well, so that the 1:39 cell:well ratio used in this experiment corresponds to 98.7% of cells deposited at an occupancy of one cell/well. 25 μl of poly(dT) magnetic beads (Invitrogen mRNA Direct Kit) were resuspended in 50 μl PBS and distributed over each PDMS slide surface, (mean of 55 poly(dT) beads per well). Magnetic beads were allowed to settle into wells by gravity for ~5 min, then a BSA-blocked dialysis membrane (12,000-14,000 MWCO regenerated cellulose, 25-mm flat width, Fisher Scientific) that had been rinsed in PBS was laid over each slide surface, sealing the microwells and trapped cells and beads inside (FIG. 1). Excess PBS was removed from the slide and membrane surfaces using a 200 μL pipette. 500 μL of cell lysis solution (500 mM LiCl in 100 mM TRIS buffer (pH 7.5) with 1% lithium dodecyl sulfate, 10 mM EDTA and 5 mM DTT) was applied to the dialysis membranes for 20 min at room temperature. Time-lapse microscopy revealed that all cells are fully lysed within 1 min (FIG. 2). Subsequently, the slides were incubated at 4° C. for 10 min at which point a Dynal MPC-S magnet was placed underneath the PDMS microwell device to hold magnetic beads inside the microwells as the dialysis membrane was removed with forceps and discarded. The PDMS slides were quickly inverted in a Petri dish containing 2 mL of cold lysis solution and the magnet was applied underneath the Petri dish to force the beads out of the microwells. Subsequently, 1 ml aliquots of the lysis solution containing resuspended beads were placed into Eppendorf tubes and beads were pelleted on a Dynal MPC-S magnetic rack and washed once without resuspension using 1 mL per tube of wash buffer 1 (100 mM Tris, pH 7.5, 500 mM LiCl, 1 mM EDTA, 4° C.). Beads were resuspended in wash buffer 1, pelleted and resuspended in wash buffer 2 (20 mM Tris, pH 7.5, 50 mM KCl, 3 mM MgCl) and pelleted again. Finally beads were suspended in 2.85 mL cold RT-PCR mixture (Quanta OneStep Fast, VWR) containing 0.05 wt % BSA (Invitrogen Ultrapure BSA, 50 mg/mL) and primer sets for VH and VL linkage amplification (FIG. 4 and Tables 6 and 10). The suspension containing the poly(dT) magnetic beads was added dropwise to a stirring IKA dispersing tube (DT-20, VWR) containing 9 mL chilled oil phase (molecular biology grade mineral oil with 4.5% Span-80, 0.4% Tween 80, 0.05% Triton X-100, v/v %, Sigma-Aldrich, St. Louis, Mo.), and the mixture was agitated for 5 min at low speed. The resulting emulsion was added to 96-well PCR plates with 100 μL emulsion per well and placed in a thermocycler. The RT step was performed under the following conditions: 30 min at 55° C., followed by 2 min at 94° C. PCR amplification was performed under the following conditions: four cycles of 94° C. for 30 s denature, 50° C. for 30 s anneal, 72° C. for 2 min extend; four cycles of 94° C. for 30 s denature, 55° C. for 30 s anneal, 72° C. for 2 min extend; 22 cycles of 94° C. for 30 s denature, 60° C. for 30 s anneal, 72° C. for 2 min extend; then a final extension step for 7 min at 72° C. After thermal cycling the emulsion was visually inspected to ensure the absence of a bulk water phase, which is a key indicator of emulsion stability. Following visual verification, the emulsion was collected and centrifuged at room temperature for 10 min at 16,000 g, the mineral oil upper phase was discarded, and 1.5 mL diethyl ether was added to extract the remaining oil phase and break the emulsion. The upper ether layer was discarded, two more ether extractions were performed and residual ether was removed in a SpeedVac for 25 min at room temperature. The aqueous phase was diluted 5:1 in DNA binding buffer and passed through a silica spin column (DNA Clean & Concentrator, Zymo Research, Irvine, Calif.) to capture the cDNA product. The column was washed twice with 300 µL wash buffer (Zymo Research Corp) and cDNA was eluted into 40 µL nuclease-free water. Finally, a nested PCR amplification was performed (ThermoPol PCR buffer with Taq Polymerase, New England Biosciences, Ipswich, Mass.) in a total volume of 200 µL using 4 µL of eluted cDNA as template with 400 nM primers (Tables 8 and 11) under the following conditions: 2 min initial denaturation at 94° C., denaturation at 94° C. for 30 s for 39 cycles, annealing at 62° C. for 30 s and extension at 72° C. for 20 s, final extension at 72° C. for 7 min. The approximately 850 bp linked product (FIG. 3) was extracted by agarose gel electrophoresis and sequenced using the 2×250 paired end MiSeq NextGen platform (Illumina, San Diego, Calif.).

TABLE 10

Primer sets for human VH and VL linkage RT-PCR amplification.

| Conc. (nM) | Primer ID |
|---|---|
| 40 | hIgA-rev-OE-AHX89 |
| 40 | hIgM-rev-OE-AHX89 |

TABLE 11

Primer sets for human VH and VL nested PCR amplification.

| Conc. (nM) | Primer ID |
|---|---|
| 400 | hIgA-all-rev-OEnested |
| 400 | hIgM-rev-OEnested |

For bioinformatic analysis, raw 2×250 MiSeq data were filtered for minimum Phred quality score of 20 over 50% of nucleotides to ensure high read quality in the CDR3-containing region (approximately HC nt 65-115 or LC nt 55-100). Sequence data were submitted to the International ImMunoGeneTics Information System (IMGT) for mapping to germline V(D)J genes (Brochet et al., 2008). Sequence data were filtered for in-frame V(D)J junctions, and productive VH and Vκ,λ sequences were paired by Illumina read ID. CDR-H3 nucleotide sequences were extracted and clustered to 96% nt identity with terminal gaps ignored, to generate a list of unique CDR-H3s in the data set. 96% nt identity cutoff was found to be the optimal cutoff to cluster sequencing error in spiked control clones; the number of unique CDR-H3 sequences and hence the number of unique V genes reported refer to the number of clusters recovered from the sample (Table 12). The top read-count CDR-L3 for each CDR-H3 cluster was assigned as a cognate pair and a list of recovered VH:VL pairs was generated. The observed accuracy ratio of 942:1 demonstrated the preservation of correct heavy and light chain pairings in the IM-9 spiked control cell line (Table 12).

TABLE 12

Key experimental statistics for Example 4.

| Immunization | Influenza (2010-11 Fluvirin) |
|---|---|
| Cell Type | Day 14 memory B cells |
| Fresh Cells vs. Freeze/Thaw | Freeze/Thaw |
| Cell:Well Ratio | 1:39 |
| % cells as single cells | 98.7% |
| Unique CDR-H3 Recovered | 240 |
| Control Cell Spike | IM-9 |
| Accuracy Ratio[1] | 942:1 |

[1]For known spiked cells, (reads correct VL):(reads top incorrect VL)

The VH:VL pairings identified using this high-throughput approach to were compared those identified using the established single-cell sorting method (Smith et al., 2009; Wrammert et al., 2008); this analysis was conducted in a double-blinded manner. Peripheral $CD19^+CD3^-CD27^+CD38^{int}$ memory B cells were isolated from a healthy volunteer 14 d after vaccination with the 2010-2011 trivalent FluVirin influenza vaccine (Smith et al., 2009). For the scRT-PCR analysis, 168 single B cells were sorted into four 96-well plates, and 168 RT and 504 nested PCR reactions were carried out individually to separately amplify the VH and VL (κ and λ) genes. DNA products were resolved by gel electrophoresis and sequenced to yield a total of 51 VH:VL pairs, of which 50 were unique. A total of 240 unique CDR-H3:CDR-L3 pairs were recovered. Four CDR-H3 sequences detected in the high-throughput pairing set were also observed in the single-cell RT-PCR analysis. A blinded analysis revealed that CDR-H3:CDR-L3 pairs isolated by the two approaches were in complete agreement (DeKosky et al., 2013). The agreement between established single-cell RT-PCR sequencing methods and the high-throughput sequencing methods demonstrated high accuracy in VH:VL sequences recovered according to the methods described in the present disclosure.

Example 5

Isolation of High Affinity Antibodies Following High-Throughput VH:VL Pairing

This example describes the isolation of high affinity anti-tetanus antibodies from human peripheral B cells following booster immunization. One female donor was booster immunized against TT/diphtheria toxoid (TD, 20 I.E. TT and 2 I.E. diphtheria toxoid, Sanofi Pasteur Merck Sharpe & Dohme GmbH, Leimen, Germany) after informed consent by the Charité Universitätsmedizin Berlin had been obtained (samples were anonymously coded and study approved by the hospital's ethical approval board, number EA1/178/11, and the University of Texas at Austin Institutional Review Board, IRB #2011-11-0095). At 7 d post TT immunization, EDTA blood was withdrawn and PBMC isolated by density gradient separation as described (Mei et al., 2009). PBMCs were stained in PBS/BSA at 4° C. for 15 min with anti-human CD3/CD14-PacB (clones UCHT1 and M5E2, respectively, Becton Dickinson, BD), CD19-PECy7 (clone SJ25C1, BD), CD27-Cy5 (clone 2E4, kind gift from René van Lier, Academic Medical Centre, University of Amsterdam, The Netherlands, labeled at the Deutsches Rheumaforschungszentrum (DRFZ), Berlin), CD20-PacO (clone HI47, Invitrogen), IgD-PerCpCy5.5 (clone L27, BD), CD38-PE (clone HIT2, BD) and TT-Digoxigenin (labeled at the DRFZ) for 15 min at 4° C. Cells were washed and a second staining was performed with anti-Digoxigenin-FITC (Roche, labeled at the DRFZ) and DAPI was added before sorting. CD19+CD3−CD14−CD38++CD27++CD20−TT+ plasmablasts were sorted using a FACSAria II sorter system (BD Biosciences). A portion of sorted cells were washed and cryopreserved in DMSO/10% FCS for high-throughput VH:VL pairing.

One vial containing approximately 2,000 frozen TT+ plasmablasts was thawed and recovered by centrifugation at 250×g for 10 min; approximately 20-30% of the cells are anticipated to be viable (Kyu et al., 2009). Cells were resuspended in 300 μL RPMI-1640 supplemented with 10% FBS, 1×GlutaMAX, 1×non-essential amino acids, 1×sodium pyruvate and 1×penicillin/streptomycin (all from Life Technologies) and incubated at 37° C. for 13 h in a 96-well plate. Recovered cells were centrifuged again at 250×g for 10 min and resuspended in 400 μL PBS, and 6 μL were withdrawn for cell counting with a hemocytometer. Cells were spiked with approximately 30 ARH-77 cells as an internal control (ATCC number CRL-1621) and VH:VL transcripts were linked as described in Example 4, omitting IgM primers and using a 38-cycle nested PCR; the resulting product was submitted for 2×250 MiSeq sequencing. VH and VL chains were also amplified individually to obtain full VH and VL sequences for antibody expression. Nested PCR product was diluted 1:9 and 0.5 μL were used as template in a PCR reaction with the following conditions: 400 nM primers (Tables 8, 11 and 13), 2 min initial denaturation at 94° C., denaturation at 94° C. for 30 s for 12 cycles, annealing at 62° C. for 30 s and extension at 72° C. for 15 s, final extension at 72° C. for 7 min. The resulting ~450 bp VH or ~400 bp VL products were purified by agarose gel electrophoresis and submitted for 2×250 MiSeq sequencing. Sequence data was processed as described above; additionally ten VH and VL pairs were selected from TT+ plasmablast pairings for antibody expression and testing. For complete antibody sequencing of these ten genes, 2×250 bp reads containing the 5′ V gene FR1-CDR2 and 3′ CDR2-FR4 were paired by Illumina read ID and consensus sequences were constructed from reads containing the exact CDR3 of interest. Antibody genes were then cloned into the human IgG expression vectors pMAZ-VH and pMAZ-VL, respectively (Mazor et al., 2007). 40 μg each of circularized ligation product were co-transfected into HEK293F cells (Invitrogen, NY, USA). Medium was harvested 6 d after transfection by centrifugation and IgG was purified by a protein-A agarose (Pierce, Ill., USA) chromatography column.

TABLE 13

Linkers for VH and VL separate amplification primers.

| Conc. (nM) | Primer ID |
| --- | --- |
| 400 | Linker-VHfwd |
| 400 | Linker-VLfwd |

Antigen affinities were determined by competitive ELISA (Friguet et al., 1985) using different concentrations of IgG in a serial dilution of antigen, ranging from 100 nM to 0.05 nM in the presence of 1% milk in PBS. Plates were coated overnight at 4° C. with 10 μg/mL of TT in 50 mM carbonate buffer, pH 9.6, washed three times in PBST (PBS with 0.1% Tween 20) and blocked with 2% milk in PBS for 2 h at room temperature. Pre-equilibrated samples of IgG with TT antigen were added to the blocked ELISA plate, incubated for 1 h at room temperature, and plates were washed 3×with PBST and incubated with 50 μl of anti-human kappa light chain-HRP secondary antibody (1:5,000, 2% milk in PBS) for ~2 min, 25° C. Plates were washed 3×with PBST, then 50 μl Ultra TMB substrate (Thermo Scientific, Rockford, Ill.) was added to each well and incubated at 25° C. for 5 min. Reactions were stopped using equal volume of 1 M $H_2SO_4$ and absorbance was read at 450 nm (BioTek, Winooski, Vt.). Each competitive ELISA replicate was fit using a four-parameter logistic (4PL) equation, with error represented as the s.d. of 2-3 replicates for each IgG analyzed. All ten antibodies showed specificity for TT and bound TT with high affinity (0.1 nM≤KD≤18 nM; Table 14) (DeKosky et al., 2013). The high affinity of anti-TT antibodies recovered demonstrates the application of high-throughput VH:VL sequencing methods in the present disclosure for antibody discovery from human cell donors.

TABLE 14

Tetanus toxoid-binding affinities of IgG isolated by high-throughput sequencing of VH:VL pairs. Affinities were calculated from competitive ELISA dilution curves.

| Antibody ID | Gene Family Assignment[1] | Affinity ($K_D$) |
| --- | --- | --- |
| TT1 | HV3-HD1-HJ6:KV3-KJ5 | 1.6 ± 0.1 nM |
| TT2 | HV3-HD3-HJ4:LV3-LJ1 | 14 ± 3 nM |
| TT3 | HV1-HD2-HJ4:KV3-KJ5 | 3.6 ± 1.8 nM |
| TT4 | HV2-HD2-HJ4:KV1-KJ1 | 2.7 ± 0.3 nM |
| TT5 | HV4-HD2-HJ6:KV2-KJ3 | 18 ± 4 nM |
| TT6 | HV1-HD3-HJ4:KV1-KJ2 | 0.57 ± 0.03 nM |
| TT7 | HV4-HD3-HJ4:KV1-KJ2 | 0.46 ± 0.01 nM |
| TT8 | HV3-HD3-HJ4:LV8-LJ3 | 2.8 ± 0.3 nM |
| TT9 | HV4-HD2-HJ4:KV1-KJ1 | 0.10 ± 0.01 nM |
| TT10 | HV1-HD3-HJ5:KV3-KJ5 | 1.6 ± 0.1 nM |

[1]Each heavy and light chain was distinct.

Example 6

Bioinformatic Identification of VH:VL Sequences Via Mutual Pairing Agreement

Examples 4 and 5 disclose the identification of correct VH:VL sequence pairs from high throughput sequencing whereby the highest read-count VL sequence for a given VH sequence revealed the native cognate VH:VL pairs encoded by individual B cells. Alternatively, this example describes a method to identify correct VH:VL pairs in high-throughput VH:VL amplicon data via consensus pairing of both VH and VL sequences.

Figure 9:
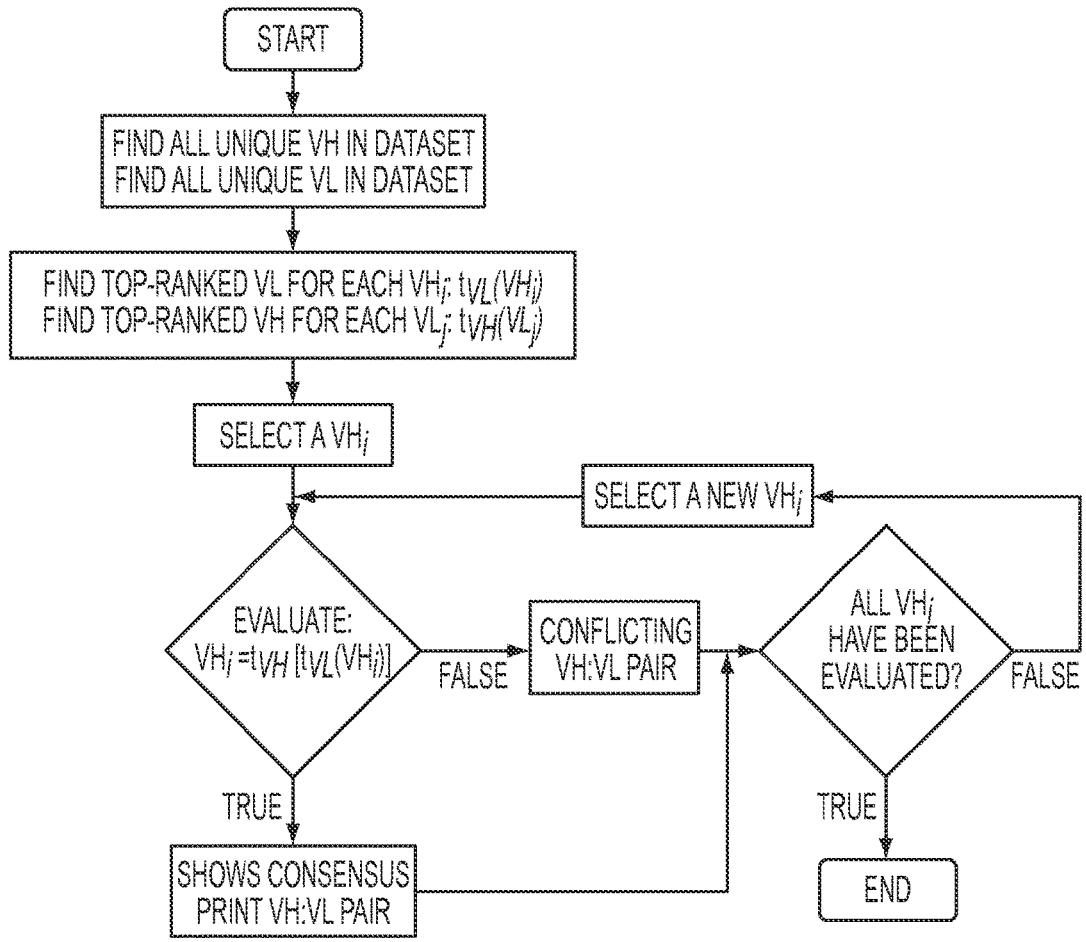
FIG. 9 shown a general decision tree algorithm for pairing of VH and VL sequences.

Raw data pairings are collected and the highest frequency VL for each VH sequence were tabulated into File 1. The top VH for every VL were tabulated separately into File 2. Many computational techniques can be used to accomplish the tabulation step; for example "grep −m 1 CDR3 filename" in Bash/Linux shell can select the top-ranked cognate pair for a CDR-H3 or CDR-L3 sequence (CDR3) from a file (filename) containing raw pairing data that has been pre-sorted to contain sequences ordered by descending read counts. Other solutions for data tabulation include the use of a hash to collect sequences and sequence read counts (e.g. Perl computing language), or the use of a dictionary to collect sequences and read counts (e.g. Python) or other data storage structures (e.g. associative memories or associative arrays). File 1 and File 2 were compared and any VH:VL pairs appearing in both files showed "consensus" in that the pair described by the top-ranked VL for a given VH agreed with the top-ranked VH for a given VL. Many computational techniques can be applied to accomplish file comparisons; one solution for file comparison uses the "join" command in Bash/Linux where lines containing desired fields that match across documents are printed to standard output. The algorithm described in the present example was effective at both identifying correct VH:VL pairs and at reducing minor sequence errors because VH:VL pairs containing sequence errors are often filtered out by mutual agreement criteria. A general decision tree of the algorithm used for pairing is provided as FIG. 9.

Example 7

VH:VL Pairing of Expanded Memory B Cells

Memory B cells were isolated and expanded in vitro, and two aliquots of the expanded cells were processed for high-throughput pairing. In vitro clonal expansion results in multiple copies of cells containing the same VH:VL pairs, thus increasing the probability of sequencing the same VH:VL pair in separate aliquots derived from the same B cell sample.

PBMC were isolated from donated human blood and stained with CD20-FITC (clone 2H7, BD Biosciences, Franklin Lakes, N.J., USA), CD3-PerCP (HIT3a, BioLegend, San Diego, Calif., USA), CD19-v450 (HIB19, BD), and CD27-APC (M-T271, BD). $CD3^-CD19^+CD20^+CD27^+$ memory B cells were incubated four days in the presence of RPMI-1640 supplemented with 10% FBS, 1×GlutaMAX, 1×non-essential amino acids, 1×sodium pyruvate and 1×penicillin/streptomycin (all from Life Technologies) along with 10 µg/mL anti-CD40 antibody (5C3, BioLegend), 1 µg/mL cPg ODN 2006 (Invivogen, San Diego, Calif., USA), 100 units/mL IL-4, 100 units/mL IL-10, and 50 ng/mL IL-21 (PeproTech, Rocky Hill, N.J., USA). 91,000 expanded B cells were seeded over 12 chips, and after a 90% estimated well seeding efficiency ratio approximately 41,000 expanded B cells were analyzed per group (1:25 cell:well ratio) according to the methods described in Example 4. Bioinformatic analysis was performed as described in Example 6. 1,033 CDR-H3 sequences with ≥1 read were sequenced in both groups, and 972/1,033 displayed matching CDR-L3 pairs to yield a 94.09% matching fraction. Pairing accuracy, $A_P$ can be estimated from the CDR-L3 matching fraction, $f_{match}$, of the two independent groups:

$$f_{match} = A_{P,Group1} \times A_{P,Group2} = A_P^2$$

$$A_P = f_{match}^{1/2}$$

which yielded an overall accuracy of 97.0%. The theoretical limit of accuracy from the rate of single cells per well by Poisson distribution (98% for the 1:25 cell:well ratio utilized in this experiment) correlated very closely with experimentally determined accuracy of VH:VL pairings.

Example 8

The Use of Leader Peptide Primers for VH:VL Pairing

In this example, primers which anneal to the leader peptide region of antibody cDNAs (as opposed to primers specific for the framework 1 of the VH and VL domains, disclosed in Example 4) were used to sequence antibody VH:VL pairs. Memory B cells were isolated from donated human PBMC, and cells were split in two groups: Group 1 consisted of 29,000 cells and was analyzed immediately (using a total of 510,000 wells, 1:16 cell:well ratio), while Group 2 was expanded as described in Example 7 and 28,000 cells were analyzed after in vitro expansion (using a total of 680,000 wells, 1:24 cell:well ratio). Both experiments were conducted as described in Example 7 using leader peptide overlap extension primers reported in Table 15 and emulsion linkage RT-PCR cycling with the following conditions: 30 min at 55° C., followed by 2 min at 94° C.; four cycles of 94° C. for 30 s denature, 54° C. for 30 s anneal, 72° C. for 2 min extend; 29 cycles of 94° C. for 30 s denature, 60° C. for 30 s anneal, 72° C. for 2 min extend; then a final extension step for 7 min at 72° C. An additional barcoded region was also included in the VL linkage primers (16N region) which was used to identify multiple sequence reads of individual linkage events (Table 15). Nested PCR was performed as in Example 5, with 25 PCR cycles for each group.

TABLE 15

Overlap extension RT-PCR primers targeting the leader peptide region of antibody mRNA.

| Conc. (nM) | Primer ID |
| --- | --- |
| 400 | CHrev-AHX89 |
| 400 | CLrev-BRH06 |
| 40 | hIgG-rev-OE-AHX89 |
| 40 | hIgA-rev-OE-AHX89 |
| 40 | hIgM-rev-OE-AHX89 |
| 40 | hIgKC-rev-OE-BRH06 |
| 40 | hIgLC-rev-OE-BRH06 |
| 40 | VH1_L |
| 40 | VH3_L |
| 40 | VH4/6_L |
| 40 | VH5_L |
| 40 | hVλ1for_L |
| 40 | hVλ2for_L |
| 40 | hVλ3for_L |
| 40 | hVλ3for-2_L |
| 40 | hVλ3for-3_L |
| 40 | hVλ4/5for_L |
| 40 | hVλ6for_L |
| 40 | hVλ7for_L |
| 40 | hVλ8for_L |
| 40 | hVκ1/2for_L |
| 40 | hVκ3for_L |
| 40 | hVκ4for_L |

After high-throughput Illumina 2×250 bp sequencing of nested PCR products, 23/23 CDR-H3 observed with ≥2 reads in both leader peptide groups displayed matching CDR-L3. This example demonstrates that various primer sets can be used to sequence multiple transcripts using the methods in the present disclosure.

Example 9

Figure 7:
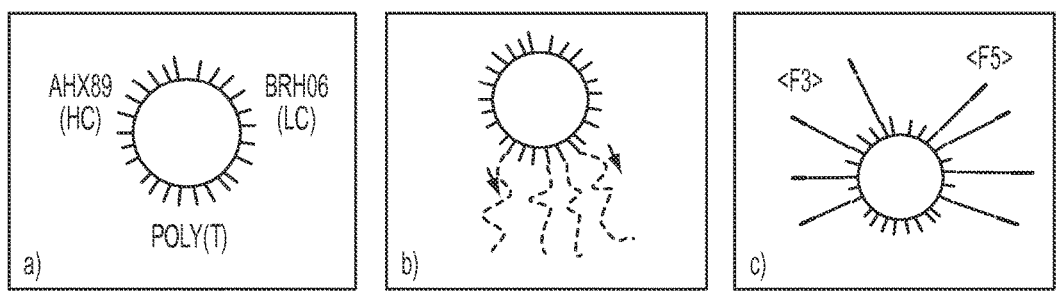
FIG. 7 shows amplification of heavy and light chain DNA on oligoimmobilized magnetic beads for high-throughput sequencing. a) Beads display a mix of 3 immobilized oligonucleotides: poly(T) for mRNA capture, AHX89 for heavy chain amplification, and BRH06 for light chain amplification. b) Reverse transcription is initiated from captured mRNA (represented by gray dashed lines) that has annealed to immobilized poly(T) oligonucleotides. Specially designed immunoglobulin constant region reverse transcription primers have either AHX89 at the 5' end (for heavy chain) or BRH06 (for light chain). Reverse transcription polymerase chain reaction occurs inside emulsion droplets. c) V region forward primers have either an <F3> sequence at the 5' end (heavy chain) or <F5> sequence (light chain) which will be used to initiate pyrosequencing. cDNA strands are displayed as black lines.
Figure 8:
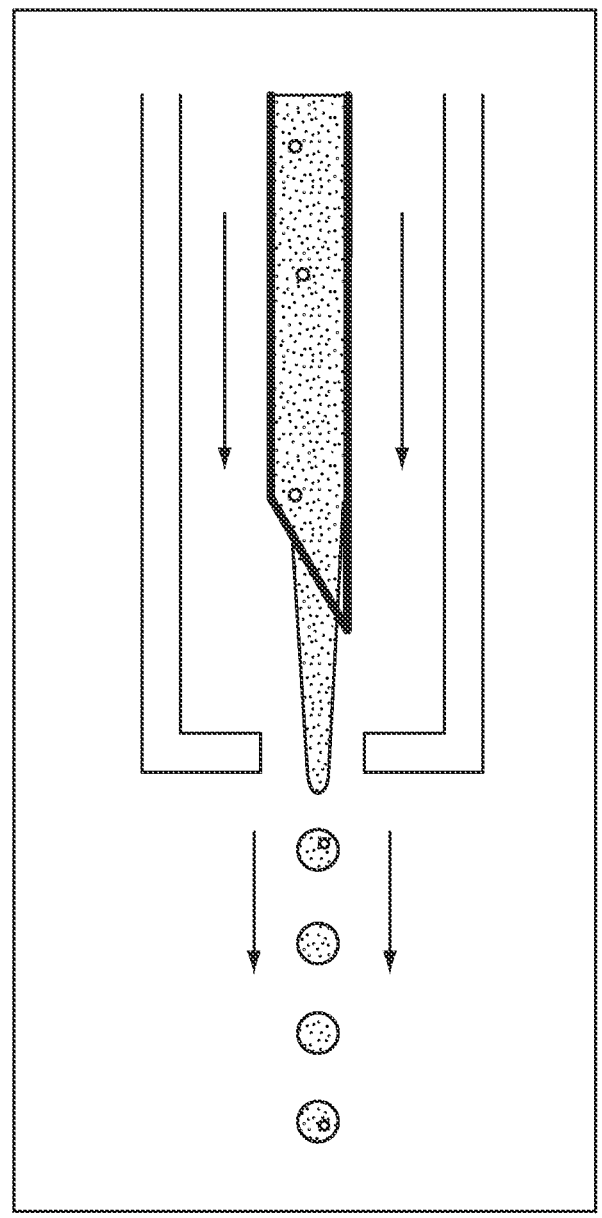
FIG. 8 shows a diagram of the nozzle/carrier stream apparatus. A glass capillary tube supplies an outer oil phase carrier stream (arrows) that surrounds a needle exit. The needle injects aqueous phase containing cells, and monodisperse droplets are generated by shear forces from annular oil phase flow.

Low Dispersity, Single Cell Water-in-Oil Droplet Formation Using a Nozzle and Annular Carrier Stream In this example, the immortalized B cell lines MOPC-21 were viably encapsulated in emulsion droplets of controlled size consisting of a mixture of cells in PBS and Trypan blue stain for cell viability visualization. This example demonstrates the isolation of single cells into emulsion droplets of controlled size distribution, furthermore the droplets being comprised of two different aqueous streams which mix immediately prior to droplet formation (FIG. 7).

Figure 5:
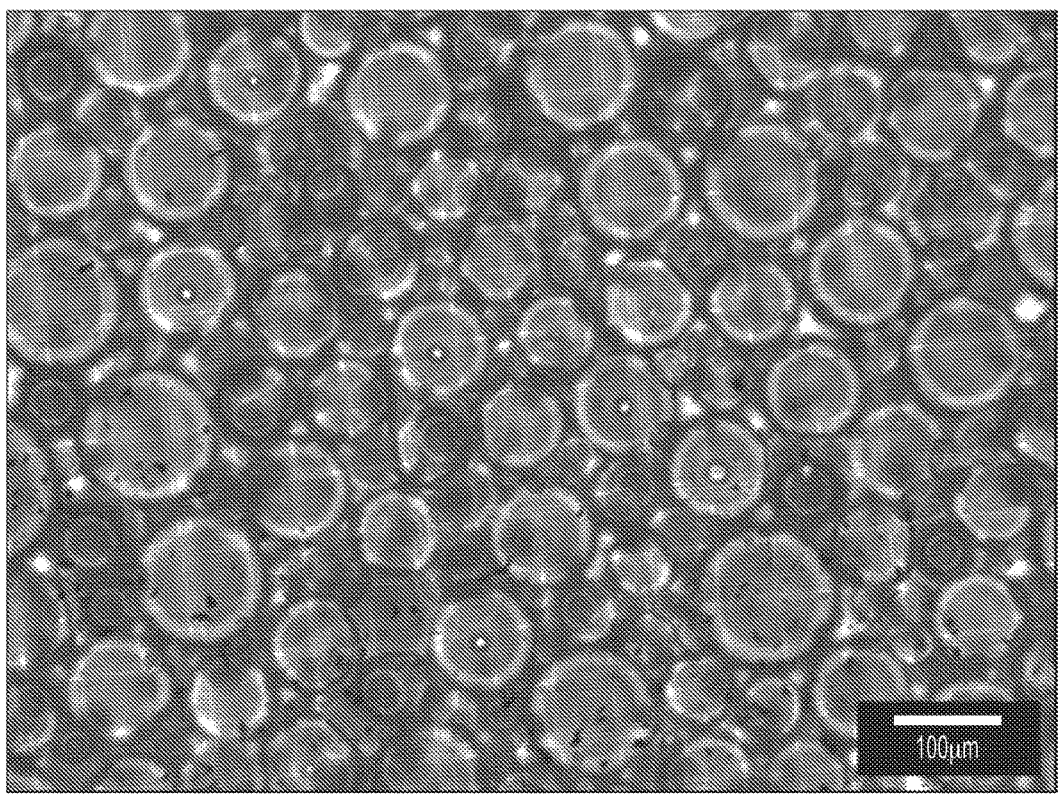
FIG. 5 shows MOPC-21 cells viably encapsulated in droplets formed via flow focusing. The two input streams to the flow focusing device were comprised of equal parts MOPC-21 cells in PBS (100,000 cells/mL, cell stream) and 0.4% trypan blue in PBS (dye stream), and the cell stream and dye streams mixed together immediately prior to the point of emulsion droplet formation. MOPC-21 cells were shown to exclude trypan blue, demonstrating viable encapsulation of single cells within the emulsion droplets.

MOPC-21 cells were resuspended at a concentration of 500,000 cells/mL of PBS. A coaxial emulsification apparatus was constructed by inserting a 26-gauge needle (Hamilton Company, Reno, Nev., USA) within 19-gauge hypodermic tubing (Hamilton) and the needle was adjusted so that the needle tip was flush with the end of the hypodermic tubing. The concentric needles were placed inside ⅜ inch OD glass tubing (Wale Apparatus, Hellertown, Pa., USA) with a 140 µm orifice such that the needle exit is approximately 2 mm from the nozzle orifice. The aqueous PBS/cell solution was injected through the needle at a rate of 500 µL/min, while a PBS/0.4% Trypan blue solution (Sigma-Aldrich, St. Louis, Mo., USA) was injected through the 19 ga hypodermic tubing, and an oil phase (molecular biology grade mineral oil with 4.5% Span-80, 0.4% Tween 80, 0.05% Triton X-100, v/v %, Sigma Aldrich Corp.) was passed through the glass tubing at a rate of 3 mL/min. Droplets suspended in oil phase were collected into a 2 mL Eppendorf tube. A syringe pump (KD Scientific Legato 200, Holliston, Mass., USA) was used to control aqueous flow rates and a gear pump (M-50, Valco Instruments, Houston, Tex., USA) was used to control oil flow rates, and the resulting emulsions were analyzed via light microscopy. Droplets with a mean diameter of approximately 85 µm were generated and encapsulated single cells displayed high viability as measured by exclusion of trypan blue (FIG. 5).

Example 10

Sequencing Multiple Transcripts in B Cells Via Encapsulation in Emulsion Droplets In this example the cell lysis and mRNA annealing to poly(T) beads was accomplished within an emulsion generated using the method outlined in Example 9. A population of memory B cells was isolated and the cells expanded as in Example 7. Memory B cells were resuspended in PBS at a concentration of 100 k/mL and passed through the innermost, 26-gauge needle of the emulsion generator device of Example 8 at a rate of 500 µL/min. 450 µL poly(dT) magnetic beads (1.0 µm diameter, New England Biosciences, Ipswich, Mass., USA) were pelleted with a magnet and resuspended in 5 mL of cell lysis/binding buffer (100 mM tris pH 7.5, 500 mM LiCl, 10 mM EDTA, 0.5% lithium dodecyl sulfate, 5 mM DTT), and the resulting mixture was passed through the 19-gauge hypodermic tubing at a rate of 500 µL/min, while oil phase (molecular biology grade mineral oil with 4.5% Span-80, 0.4% Tween 80, 0.05% Triton X-100, v/v %, Sigma Aldrich Corp.) was passed through the outermost glass tubing at a rate of 3 mL/min to generate an emulsion consisting of aqueous droplets of approximately 85 µm diameter containing single cells. The emulsion stream was collected into 2 mL Eppendorf tubes, and cells were lysed by detergent as droplets were generated to allow for mRNA capture onto poly(dT) magnetic beads encapsulated within the emulsion droplets.

Each 2 mL emulsion tube was maintained at room temperature for three minutes before being placed on ice for a minimum of ten minutes. Then the tubes were centrifuged at 16,000×g for 5 minutes at 4° C., and the upper mineral oil layer was removed and discarded. 200 µL of cold diethyl ether was added to chemically break the emulsion and the tubes were centrifuged at 16,000×g for 2.5 minutes to pellet magnetic beads. Magnetic beads were withdrawn using a pipette, pelleted, and resuspended in 2 mL lysis/binding buffer (100 mM tris pH 7.5, 500 mM LiCl, 10 mM EDTA, 0.5% LiDS, 5 mM DTT). Beads were then washed and resuspended in OE RT-PCR mixture as in Example 8. Leader peptide primers were used, primer concentrations are given in Table 15. The OE RT-PCR mixture bead suspension was emulsified and thermally cycled, cDNA was extracted, and a nested PCR was performed (see Example 8). Nested PCR product was electrophoresed to purify linked transcripts, which were then sequenced as in Example 8 above.

After high-throughput Illumina 2×250 bp sequencing of nested PCR products, 14,121 VH:VL pairs with ≥2 reads were recovered according to the algorithm described in Example 6 (7,367 VH:VL pairs in Group 1, and 6,754 pairs in Group 2). 3,935 CDR-H3 were observed with ≥2 reads in both groups. 3,899/3,935 of CDR-H3 observed in both groups displayed matching CDR-L3, indicating 99.5% overall accuracy according to the formula outlined in Example 7. The present example demonstrates the sequencing of multiple transcripts via mRNA capture from single cells isolated within emulsion droplets.

Example 11

Parallel Sequencing of Heavy and Light Chain cDNAs from Single Cells

Previous examples demonstrated the use of magnetic beads to capture mRNA and covalent linkage of desired cDNAs from a single cell (e.g., VH and VL cDNAs) to create a single amplicon. The single VH-VL amplicons thus generated were sequenced by high throughput DNA sequencing to reveal the repertoire of naturally paired VH and VL sequences.

In the example, the cDNAs captured onto beads were sequenced directly without linking (i.e. without creating a linked VH-VL amplicon). In this manner, the identity of the desired transcripts from a single cell was revealed without the need for overlap extension PCR. First, an equal mixture of three 5'-amine functionalized primers (Table 17) was conjugated to functionalized magnetic beads so that the immobilized oligonucleotides on each magnetic bead were in the following proportion: ⅓ poly(T) for mRNA capture, ⅓ primer specific for desired transcript 1 (e.g., the AHX89 primer of Table 1), and ⅓ primer specific for desired transcript 2 (Table 17). These primer-conjugated magnetic beads served a dual purpose: first, upon lysis, poly(T) primers captured heavy and light chain mRNA from individual cells, as in Examples 4-6; second, in the emulsion RT-PCR step, AHX89 and BRH06 primers caused heavy and light chain cDNA to amplify on the bead surface. After RT-PCR, magnetic beads were used as sequencing template for high-throughput sequencing. The process is outlined in FIG. 7.

An equal mixture of three 5'-amine oligonucleotides (Table 16) was immobilized to functionalized magnetic beads according to manufacturer protocols (Dynal MyOne Carboxylic Acid beads, 1.0 µm diameter, Invitrogen Corp.). Then, a mixture of MOPC-21 and MOPC-315 immortalized cells were washed and suspended at 100,000 cells/mL in PBS (pH 7.4). 1.2×10⁸ functionalized magnetic beads were added per mL of cell lysis/mRNA binding solution, as outlined in Example 10. The cell/bead suspension was emulsified as in Example 10, cells are lysed and mRNA anneals to beads. Then beads were recovered by breaking the emulsion, washed as described in Example 10, and emulsion RT-PCR was performed. RT-PCR primer concentrations are given in Table 17. Cycling conditions were as follows: 30 min at 55° C., followed by 2 min at 94° C.; four cycles of 94° C. for 30 s denature, 57° C. for 1 min anneal, 72° C. for 2 min extend; 29 cycles of 94° C. for 30 s denature, 59° C. for 30 s anneal, 72° C. for 2 min extend; then a final extension step for 7 min at 72° C.

TABLE 16

Primers conjugated to the magnetic bead surface.

| Conc. | Primer ID |
| --- | --- |
| 33% | oligodT(25)-5'amine |
| 33% | CHrev-AHX89-5'amine |
| 33% | CLrev-BRH06-5'amine |

TABLE 17

Primers in the MOPC-21/MOPC-315 RT-PCR mix.

| Conc. | Primer ID |
| --- | --- |
| 400 | CHrev-AHX89 |
| 400 | CLrev-BRH06 |
| 40 | MOPC21-CHrev-AHX89 |
| 40 | MOPC21-CLrev-BRH06 |
| 40 | MOPC315-CLrev-BRH06 |
| 40 | MOPC315-CHrev-AHX89 |
| 400 | MOPC21-VH-OE-5'<F3> |
| 400 | MOPC21-VL-OE-5'<F5> |
| 400 | MOPC315-VH-OE-5'<F3> |
| 400 | MOPC315-VL-OE-5'<F5> |

After emulsion RT-PCR, the emulsion was broken with n-butanol according to SOLiD gene sequencing manufacturer protocols (Applied Biosystems), and magnetic beads were submitted as direct template for the Ion Torrent sequencing platform (Life Technologies). Sequencing was initiated first with the <F3> heavy chain primer to collect heavy chain cDNA sequences, followed by sequencing with the <F5> light chain primer to collect light chain cDNA sequences. The heavy and light chain sequences were matched by location on the Ion Torrent sequencing platform to obtain the native heavy and light chain pairings.

Example 12

Sequencing of Paired VH:VL Transcripts from Cells Encoding High-Affinity Antibodies Previous examples detailed the use of various techniques for sequencing multiple transcripts from a variety of cell populations. The present example describes a method for high-throughput sequencing natively paired VH:VL antibody sequences from only cells encoding high affinity antibodies specific to a particular antigen of interest using antigen-dependent poly(dT) capture and subsequent VH:VL sequencing.

Antigen-coated magnetic beads were prepared by covalently coupling free vaccine-grade tetanus toxoid (TT) (1 mM oligonucleotide, 40 nM TT, Statens Serum Institut, Copenhagen, Denmark) to carboxylic acid-functionalized magnetic beads (1 μm diameter Dynal MyOne COOH beads, Life Technologies) according to manufacturer protocols.

PBMC were collected from donated blood 14 d after administration of tetanus toxoid (TT)/diphteria toxoid boost vaccination (TD; 20 I.E. TT and 2 I.E. diphteria toxoid, Sanofi Pasteur MSD GmbH, Leimen, Germany) and sorted via labeled antibody staining and FACS sorting, as in Example 7. Memory B cells were seeded into sterile PDMS slides as described in Example 4 along with antigen-coated beads (approximately 40 beads/well), and cells were sealed inside the wells using a dialysis membrane and cultured inside the PDMS microwell slides for four days in memory B cell stimulation media: RPMI-1640 supplemented with 10% immunoglobulin-depleted FBS, 1×GlutaMAX, 1×non-essential amino acids, 1×sodium pyruvate and 1×penicillin/streptomycin (all from Life Technologies) along with 10 μg/mL anti-CD40 antibody (5C3, BioLegend), 500 U/ml IL-4, and 5 ng/ml IL-5 (PeproTech, Rocky Hill, N.J., USA). During this time, the cells were stimulated to secrete antibody (Taubenheim et al., 2012), and any secreted antibody specific to TT became bound to magnetic microbeads containing immobilized antigen.

A solution of 5' streptavidin-labeled poly(dT)$_{25}$ oligonucleotides (Integrated DNA Technologies, USA) was mixed in an equimolar ratio with goat anti-human IgG-biotin conjugate (B1140, Sigma-Alrich, USA). The streptavidin and biotin associated in solution to form anti-IgG antibodies with tethered poly(dT)$_{25}$ oligonucleotides for mRNA capture. After four days in culture, the seal was broken and the slide surface was washed gently with 400 μL PBS three times to wash away secreted antibodies without disturbing cells and beads inside wells. Excess PBS was removed and 350 μL of RPMI-1640 media containing 10 nM anti-IgG antibody/poly(dT)$_{25}$ conjugate was added to the microwell slide surface and the slide was incubated at room temp for 45 minutes. Over the course of the 45 min incubation, any antigen-labeled microbeads which had been coated by anti-TT antibodies following the 4-day secretion phase (ie antigen-labeled microbeads co-localized in a well with a secreting cell that encoded a specific antibody for TT) became decorated with poly(dT)$_{25}$ for mRNA capture. Subsequently the slides were gently washed three times with 400 uL PBS to remove excess antibody/oligonucleotide conjugate and microwells were sealed with a dialysis membrane, cells were lysed, beads were recovered with a magnet, and emulsion linkage RT-PCR was performed as in NEW Example 3, with the exception that 0.1% lithium dodecyl sulfate was used in the cell lysis buffer instead of 1% lithium dodecyl sulfate. Nested PCR was performed and linked transcripts were sequenced using a long-read Next Generation sequencing platform, as in NEW Example 5.

The process outlined in the present method enriched the sequence set for high-affinity antigen-specific VH:VL pairs, as only the antigen-labeled beads with bound IgG immunoglobulin contained the poly(dT)$_{25}$ sequence required for mRNA capture after cell lysis. Thus, the method outlined in this example demonstrates the application of the high-throughput VH:VL pairings technique for sequencing of a large number of antigen-specific VH:VL pairs in a single experiment without the need for surface expression of immunoglobulin.

Example 13

RT-PCR on Single Cells Emulsified Using a Low Dispersity Droplet Emulsion

As in Example 6, an emulsion was formed by injecting aqueous stream out of a nozzle into a fast-moving annular oil phase. Shear forces generated by the carrier stream induced aqueous droplet formation with a tightly controlled size distribution, and the nozzle/carrier stream method generated emulsions of monodisperse droplet sizes which reduces the incidence of multiple cells per emulsion droplet caused by a range of droplet sizes. In this example, a mixture of two immortalized cell lines (MOPC-21 and MOPC-315) was used to demonstrate cell encapsulation and linkage RT-PCR directly in emulsion droplets of approximately 4 nL volume without intermediate cell lysis or mRNA capture steps.

An equal mix of RNAse-treated and washed MOPC-21 and MOPC-315 cells (as in Example 2) were resuspended at a concentration of 50,000 total cells/mL in PBS, while another aqueous phase was prepared consisting of 2×concentrated RT-PCR mixture (Quanta OneStep Fast qRT-PCR) with 0.1% BSA (Invitrogen Ultrapure BSA, 50 mg/mL), 4% SuperAse In RNAse inhibitor (Invitrogen, USA), and 0.1% NP-40 detergent. An emulsification apparatus was prepared as in Example 10. All needles and needle supply tubes were pre-blocked in 1% BSA for 30 minutes and rinsed with PBS, and cells in PBS were delivered through the inner (26 gauge) needle while RT-PCR mixture and detergent was delivered via the outer (19 gauge) needle, with both aqueous phases being 500 µL/min. Oil carrier phase (molecular biology grade mineral oil with 4.5% Span-80, 0.4% Tween 80, 0.05% Triton X-100, v/v %, oil phase reagents from Sigma Aldrich Corp.) flowed through the outer glass tubing at a rate of 3 mL/min and samples were collected as in Example 10. A total of 2 mL of the cell/RT-PCR mixture mixed with 2 mL of NP-40 diluent was emulsified for approximately 100,000 cells analyzed. Primer concentrations for the RT-PCR mixture are given in Table 1, with the same thermal cycling conditions being used as those in Example 11.

The cell emulsion for RT-PCR was then placed into 96-well plates and thermally cycled, cDNA was extracted, and a nested PCR reaction was performed (see Example 4). Nested PCR primers are given in Table 2, and thermal cycling conditions for the PCR were as follows: a 2 min denaturing step at 94° C., followed by thermal cycling at 94° C. for 30 s denature, 62° C. for 30 s anneal, 72° C. for 20 s extend, for 30 cycles. Nested PCR product was electrophoresed to purify linked VH-VL cDNA, which was submitted as template for NextGen sequencing.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

\*\*\*

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Brochet, X., Lefranc, M.-P. & Giudicelli, V. IMGT/V-QUEST: the highly customized and integrated system for IG and TR standardized V-J and V-D-J sequence analysis. *Nucleic Acids Res.* 36, W503-W508 (2008).

Chan, M. et al. Evaluation of Nanofluidics Technology for High-Throughput SNP Genotyping in a Clinical Setting. *J Mol Diagn* 13, 305-312 (2011).

Citri, A. et al. Comprehensive qPCR profiling of gene expression in single neuronal cells. *Nature Protocols* 7, 118-127 (2012).

DeKosky, B. J. et al. High-throughput sequencing of the paired human immunoglobulin heavy and light chain repertoire. *Nat Biotech* 31, 166-169 (2013).

Friguet, B., Chaffotte, A. F., Djavadi-Ohaniance, L. & Goldberg, M. E. Measurements of the true affinity constant in solution of antigen-antibody complexes by enzyme-linked immunosorbent assay. *Journal of Immunological Methods* 77, 305-319 (1985).

Kojima, T. et al. PCR amplification from single DNA molecules on magnetic beads in emulsion: application for high-throughput screening of transcription factor targets. *Nucleic Acids Res.* 33 (2005).

Krause, J. C. et al. Epitope-Specific Human Influenza Antibody Repertoires Diversify by B Cell Intraclonal Sequence Divergence and Interclonal Convergence. *The Journal of Immunology* 187, 3704-3711 (2011).

Kyu, S. Y. et al. Frequencies of human influenza-specific antibody secreting cells or plasmablasts post vaccination from fresh and frozen peripheral blood mononuclear cells. *Journal of Immunological Methods* 340, 42-47 (2009).

Mar, J. C. et al. Inferring steady state single-cell gene expression distributions from analysis of mesoscopic samples. *Genome Biol* 7 (2006).

Mary, P. et al. Analysis of gene expression at the single-cell level using microdroplet-based microfluidic technology. *Biomicrofluidics* 5 (2011).

Mazor, Y., Barnea, I., Keydar, I. & Benhar, I. Antibody internalization studied using a novel IgG binding toxin fusion. *Journal of Immunological Methods* 321, 41-59 (2007).

Mei, H. E. et al. Blood-borne human plasma cells in steady state are derived from mucosal immune responses. *Blood* 113, 2461-2469 (2009).

Meijer, P. et al. Isolation of human antibody repertoires with preservation of the natural heavy and light chain pairing. *Journal of molecular biology* 358, 764-772 (2006).

Novak, R. et al. Single-Cell Multiplex Gene Detection and Sequencing with Microfluidically Generated Agarose Emulsions. *Angew. Chem.-Int. Edit.* 50, 390-395 (2011).

Reddy, S. T. et al. Monoclonal antibodies isolated without screening by analyzing the variable-gene repertoire of plasma cells. *Nature biotechnology* 28, 965-U920 (2010).

Sanchez-Freire, V. et al. Microfluidic single-cell real-time PCR for comparative analysis of gene expression patterns. *Nat. Protocols* 7, 829-838 (2012).

Smith, K. et al. Rapid generation of fully human monoclonal antibodies specific to a vaccinating antigen. *Nat. Protocols* 4, 372-384 (2009).

Taubenheim, N. et al. High Rate of Antibody Secretion Is not Integral to Plasma Cell Differentiation as Revealed by XBP-1 Deficiency. *The Journal of Immunology* 189, 3328-3338 (2012).

Toriello, N. M. et al. Integrated microfluidic bioprocessor for single-cell gene expression analysis. *Proc Natl Acad Sci USA* 105, 20173-20178 (2008).

White, A. K. et al. High-throughput microfluidic single-cell RT-qPCR. *Proc Natl Acad Sci USA* (2011).

Wrammert, J. et al. Rapid cloning of high-affinity human monoclonal antibodies against influenza virus. *Nature* 453, 667-671 (2008).

Wu, X. et al. Focused Evolution of HIV-1 Neutralizing Antibodies Revealed by Structures and Deep Sequencing. *Science* 333, 1593-1602 (2011).

What is claimed is:

1. A method comprising:
    a) sequestering single cells and an mRNA capture agent into individual compartments;
    b) lysing the cells and collecting mRNA transcripts with the mRNA capture agent;
    c) isolating the mRNA from the compartments using the mRNA capture agent;
    d) performing reverse transcription followed by PCR amplification on the captured mRNA; and
    e) sequencing at least two distinct cDNA products amplified from a single cell,
    wherein:
        (i) the at least two distinct cDNA products comprise paired antibody VH and VL sequences, wherein the cells are B-cells; or
        (ii) the at least two distinct cDNA products comprise paired T-cell receptor sequences, wherein the cells are T-cells.

2. The method of claim 1, wherein the at least two distinct cDNA products comprise paired antibody VH and VL sequences, wherein the cells are B-cells.

3. The method of claim 1, wherein the mRNA capture agent is a bead.

4. The method of claim 3, wherein the beads are magnetic.

5. The method of claim 3, wherein the bead comprises oligonucleotides which hybridize mRNA.

6. The method of claim 5, wherein the oligonucleotides comprise at least one of poly(T) and primers specific to a transcript of interest.

7. The method of claim 2, wherein the paired antibody VH and VL sequences are for an antibody that binds to an antigen of interest.

8. The method of claim 5, wherein the beads are conjugated to an antigen of interest and the oligonucleotides are only conjugated to the beads in the presence of an antibody that binds to the antigen of interest.

9. The method of claim 1, wherein the individual compartments are wells in a gel or microtiter plate.

10. The method of claim 1, said individual compartments having a volume of less than 5 nL.

11. The method of claim 10, wherein the compartments are sealed with a permeable membrane prior to step (c).

12. The method of claim 1, wherein the individual compartments are microvesicles in an emulsion.

13. The method of claim 1, wherein steps (a) and (b) are performed concurrently.

14. The method of claim 1, wherein steps (a) and (b) comprise isolating single cells and an mRNA capture agent into individual microvesicles in an emulsion and in the presence of a cell lysis solution.

15. The method of claim 2, comprising obtaining sequences from at least 10,000 individual cells or at least 5,000 individual paired antibody VH and VL sequences.

16. The method of claim 1, wherein step (e) comprises:
    linking VH and VL cDNAs by performing overlap extension reverse transcriptase polymerase chain reaction to link VH and VL cDNAs in single DNA molecules, wherein the at least two distinct cDNA products comprise paired antibody VH and VL sequences.

17. The method of claim 1, wherein step (e) does not comprise the use of overlap extension reverse transcriptase polymerase chain reaction.

18. The method of claim 2, wherein the VH and VL sequences are obtained by sequencing of distinct molecules.

19. The method of claim 1, wherein the at least two distinct cDNA products comprise paired T-cell receptor sequences, wherein the cells are T-cells.

20. The method of claim 1, wherein step (e) comprises linking cDNA by performing overlap extension reverse transcriptase polymerase chain reaction to link at least 2 transcripts into a single DNA molecule.

* * * * *